US010927364B2

(12) United States Patent
Salmon et al.

(10) Patent No.: US 10,927,364 B2
(45) Date of Patent: Feb. 23, 2021

(54) HEAT-STABLE METAGENOMIC CARBONIC ANHYDRASES AND THEIR USE

(71) Applicant: Novozymes A/S, Bagsvaerd (DK)

(72) Inventors: Sonja Salmon, Raleigh, NC (US); Martin Simon Borchert, Hilleroed (DK); Thomas Holberg Blicher, Copenhagen (DK); Wolfgang Streit, Monkeberg (DE); Mirjam Perner, Hamburg (DE)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/318,672

(22) PCT Filed: Jul. 20, 2017

(86) PCT No.: PCT/US2017/042994
§ 371 (c)(1),
(2) Date: Jan. 17, 2019

(87) PCT Pub. No.: WO2018/017792
PCT Pub. Date: Jan. 25, 2018

(65) Prior Publication Data

US 2019/0241881 A1 Aug. 8, 2019

(30) Foreign Application Priority Data

Jul. 20, 2016 (EP) .................................... 16180365

(51) Int. Cl.
*C12N 9/88* (2006.01)
*B01D 53/84* (2006.01)

(52) U.S. Cl.
CPC ............... *C12N 9/88* (2013.01); *B01D 53/84* (2013.01); *C12Y 402/01001* (2013.01); *B01D 2255/804* (2013.01); *C07K 2319/02* (2013.01)

(58) Field of Classification Search
CPC .......................... C12N 9/88; C12Y 402/01001
USPC .......................................................... 435/232
See application file for complete search history.

(56) References Cited

FOREIGN PATENT DOCUMENTS

| | | | | |
|---|---|---|---|---|
| KR | 20140139787 | | 5/2013 | |
| WO | 2010151787 A1 | | 12/2010 | |
| WO | 2012025577 A1 | | 3/2012 | |
| WO | WO-2012025577 A1 | * | 3/2012 | ............... C12N 9/88 |

OTHER PUBLICATIONS

Perner et al, In situ chemistry and microbial community compositions in five deep-sea hydrothermal fluid samples from Irina II in the Logatchev field. Environmental Microbiology (2013) 15(5), 1551-1560.*
Borchert, WO2012025577 SID1. Alignment with SID2 herein. (Year: 2012).*
Anantharaman et al, 2016, ISME Journal 10(1), 225-239.
Christianson et al, 1996, Acc chem res 29, 331-339.
Favre et al, 2009, J Mol CatalB Enzym 60(3-4), 163-170.
Fiore et al, 2015, International journal of molecular sciences 16(7), 15456-15480.
Hewett-Emmett et al, 1996, Molecular physogenetics and evolution 5(1), 50-77.
James et al, 2014, Acta Cryst Section D70, 2607-2618.
Nishimori et al, 2007, Bioorg Med Chem 15, 6742-6747.
Pena et al, 2010, PNAS 107, 2455-2460.
Perner et al, 2013, Environmental Microbiology 15(5), 1551-1560.
Supuran et al, 2004, CRC Press LLC.
Xu et al, 2008, Nature 542, 56-61.

* cited by examiner

*Primary Examiner* — Sheridan Swope
(74) *Attorney, Agent, or Firm* — Eric J. Fechter

(57) ABSTRACT

The present invention relates to polypeptides having carbonic anhydrase activity and polynucleotides encoding the polypeptides. The invention also relates to nucleic acid constructs, vectors, and host cells comprising the polynucleotides as well as methods of producing and using the polypeptides.

15 Claims, 2 Drawing Sheets

Specification includes a Sequence Listing.

SEQUENCE LISTING

```
<160> NUMBER OF SEQ ID NOS: 9

<210> SEQ ID NO 1
<211> LENGTH: 735
<212> TYPE: DNA
<213> ORGANISM: Artificial
<220> FEATURE:
<223> OTHER INFORMATION: Metagenomic sequence
<220> FEATURE:
<221> NAME/KEY: CDS
<222> LOCATION: (1)..(732)
<220> FEATURE:
<221> NAME/KEY: sig_peptide
<222> LOCATION: (1)..(54)
<220> FEATURE:
<221> NAME/KEY: mat_peptide
<222> LOCATION: (55)..(732)

<400> SEQUENCE: 1

atg aag aaa ctt gca ttt att atc ttc tca ctg aca att gga aca gtt       48
Met Lys Lys Leu Ala Phe Ile Ile Phe Ser Leu Thr Ile Gly Thr Val
            -15                 -10                 -5

att gcg gga gga gta ggc cac tgg agt tat cac gga gaa aca ggt cca       96
Ile Ala Gly Gly Val Gly His Trp Ser Tyr His Gly Glu Thr Gly Pro
    -1  1               5                   10

cag cac tgg gga gac ctt aaa aat gag tat atc atg tgt aaa atc ggg      144
Gln His Trp Gly Asp Leu Lys Asn Glu Tyr Ile Met Cys Lys Ile Gly
15                  20                  25                  30

aaa aat cag tct cct gtt gac atc tca cga ata gtt gag gca gag ttg      192
Lys Asn Gln Ser Pro Val Asp Ile Ser Arg Ile Val Glu Ala Glu Leu
                35                  40                  45

gaa aaa atc aaa ata aac tac tcc agt ggt gga agc tcc ata aca aat      240
Glu Lys Ile Lys Ile Asn Tyr Ser Ser Gly Gly Ser Ser Ile Thr Asn
            50                  55                  60

aat ggc cac act ata aag gtc agc tac gaa ccg gga agc tat att att      288
Asn Gly His Thr Ile Lys Val Ser Tyr Glu Pro Gly Ser Tyr Ile Ile
        65                  70                  75

gtt gac ggt att cgt ttt gag ctg aaa cag ttt cac ttc cat gca cca      336
Val Asp Gly Ile Arg Phe Glu Leu Lys Gln Phe His Phe His Ala Pro
    80                  85                  90

agt gaa cac aca ata aaa ggt aag tct tat cct ttt gaa gct cac ttt      384
Ser Glu His Thr Ile Lys Gly Lys Ser Tyr Pro Phe Glu Ala His Phe
95                  100                 105                 110

gtt cac gca gac aaa gac ggt aat ctg gct gta att ggt gtg att ttc      432
Val His Ala Asp Lys Asp Gly Asn Leu Ala Val Ile Gly Val Ile Phe
                115                 120                 125

aaa gag gga aag aaa aac cca att att gag aag ata tgg gaa aac ctg      480
Lys Glu Gly Lys Lys Asn Pro Ile Ile Glu Lys Ile Trp Glu Asn Leu
            130                 135                 140

cct gaa gct gga aaa aca atc aaa ctt gct cac aaa ata aat gct tat      528
Pro Glu Ala Gly Lys Thr Ile Lys Leu Ala His Lys Ile Asn Ala Tyr
```

-continued

```
        145                 150                 155

gac ctt tta cct aaa aaa aag aag tac tac aga tac agt ggc tct tta      576
Asp Leu Leu Pro Lys Lys Lys Lys Tyr Tyr Arg Tyr Ser Gly Ser Leu
    160                 165                 170

aca act cct cca tgt tct gaa ggt gta aga tgg att gtg atg gaa gag      624
Thr Thr Pro Pro Cys Ser Glu Gly Val Arg Trp Ile Val Met Glu Glu
175                 180                 185                 190

gaa atg gaa ctt tct aaa gag cag att gag aaa ttc aga aaa ctg atg      672
Glu Met Glu Leu Ser Lys Glu Gln Ile Glu Lys Phe Arg Lys Leu Met
                195                 200                 205

gga gga gat acc aac aga cct gtg caa cca ctg aac gca agg atg att      720
Gly Gly Asp Thr Asn Arg Pro Val Gln Pro Leu Asn Ala Arg Met Ile
            210                 215                 220

atg gaa atg gat taa                                                  735
Met Glu Met Asp
        225


<210> SEQ ID NO 2
<211> LENGTH: 244
<212> TYPE: PRT
<213> ORGANISM: Artificial
<220> FEATURE:
<223> OTHER INFORMATION: Synthetic Construct

<400> SEQUENCE: 2

Met Lys Lys Leu Ala Phe Ile Ile Phe Ser Leu Thr Ile Gly Thr Val
            -15                 -10                 -5

Ile Ala Gly Gly Val Gly His Trp Ser Tyr His Gly Glu Thr Gly Pro
    -1  1               5                   10

Gln His Trp Gly Asp Leu Lys Asn Glu Tyr Ile Met Cys Lys Ile Gly
15                  20                  25                  30

Lys Asn Gln Ser Pro Val Asp Ile Ser Arg Ile Val Glu Ala Glu Leu
                35                  40                  45

Glu Lys Ile Lys Ile Asn Tyr Ser Ser Gly Gly Ser Ser Ile Thr Asn
            50                  55                  60

Asn Gly His Thr Ile Lys Val Ser Tyr Glu Pro Gly Ser Tyr Ile Ile
        65                  70                  75

Val Asp Gly Ile Arg Phe Glu Leu Lys Gln Phe His Phe His Ala Pro
    80                  85                  90

Ser Glu His Thr Ile Lys Gly Lys Ser Tyr Pro Phe Glu Ala His Phe
95                  100                 105                 110

Val His Ala Asp Lys Asp Gly Asn Leu Ala Val Ile Gly Val Ile Phe
                115                 120                 125

Lys Glu Gly Lys Lys Asn Pro Ile Ile Glu Lys Ile Trp Glu Asn Leu
            130                 135                 140

Pro Glu Ala Gly Lys Thr Ile Lys Leu Ala His Lys Ile Asn Ala Tyr
        145                 150                 155

Asp Leu Leu Pro Lys Lys Lys Lys Tyr Tyr Arg Tyr Ser Gly Ser Leu
    160                 165                 170

Thr Thr Pro Pro Cys Ser Glu Gly Val Arg Trp Ile Val Met Glu Glu
175                 180                 185                 190

Glu Met Glu Leu Ser Lys Glu Gln Ile Glu Lys Phe Arg Lys Leu Met
                195                 200                 205

Gly Gly Asp Thr Asn Arg Pro Val Gln Pro Leu Asn Ala Arg Met Ile
            210                 215                 220

Met Glu Met Asp
        225
```

```
<210> SEQ ID NO 3
<211> LENGTH: 762
<212> TYPE: DNA
<213> ORGANISM: Artificial
<220> FEATURE:
<223> OTHER INFORMATION: Codon optimized gene with signal peptide
<220> FEATURE:
<221> NAME/KEY: CDS
<222> LOCATION: (1)..(759)
<220> FEATURE:
<221> NAME/KEY: sig_peptide
<222> LOCATION: (1)..(81)
<220> FEATURE:
<221> NAME/KEY: mat_peptide
<222> LOCATION: (82)..(759)

<400> SEQUENCE: 3

atg aag aaa ccg ttg ggg aaa att gtc gca agc acc gca cta ctc att       48
Met Lys Lys Pro Leu Gly Lys Ile Val Ala Ser Thr Ala Leu Leu Ile
        -25                 -20                 -15

tct gtt gct ttt agt tca tcg ata gca tca gca ggc gga gtt ggc cat       96
Ser Val Ala Phe Ser Ser Ser Ile Ala Ser Ala Gly Gly Val Gly His
    -10                 -5              -1  1               5

tgg tca tat cat ggc gaa aca gga ccg caa cat tgg gga gat ctg aaa      144
Trp Ser Tyr His Gly Glu Thr Gly Pro Gln His Trp Gly Asp Leu Lys
            10                  15                  20

aat gaa tac atc atg tgc aaa atc ggc aaa aat caa tca ccg gtc gat      192
Asn Glu Tyr Ile Met Cys Lys Ile Gly Lys Asn Gln Ser Pro Val Asp
            25                  30                  35

att agc aga att gtt gaa gca gaa ctg gaa aaa atc aaa atc aac tat      240
Ile Ser Arg Ile Val Glu Ala Glu Leu Glu Lys Ile Lys Ile Asn Tyr
        40                  45                  50

tca tca ggc gga agc agc att aca aat aac ggc cat aca atc aaa gtc      288
Ser Ser Gly Gly Ser Ser Ile Thr Asn Asn Gly His Thr Ile Lys Val
    55                  60                  65

agc tat gaa ccg gga agc tat att atc gtt gat ggc att cgc ttt gaa      336
Ser Tyr Glu Pro Gly Ser Tyr Ile Ile Val Asp Gly Ile Arg Phe Glu
70                  75                  80                  85

ctg aaa cag ttt cat ttt cat gca ccg agc gaa cat acg att aaa ggc      384
Leu Lys Gln Phe His Phe His Ala Pro Ser Glu His Thr Ile Lys Gly
                90                  95                  100

aaa tca tat ccg ttt gaa gcg cat ttt gtt cat gca gat aaa gat ggc      432
Lys Ser Tyr Pro Phe Glu Ala His Phe Val His Ala Asp Lys Asp Gly
            105                 110                 115

aat ctg gca gtt att ggc gtc atc ttt aaa gaa ggc aaa aaa aac ccg      480
Asn Leu Ala Val Ile Gly Val Ile Phe Lys Glu Gly Lys Lys Asn Pro
        120                 125                 130

atc atc gaa aaa atc tgg gaa aat ctg ccg gaa gca ggc aaa aca att      528
Ile Ile Glu Lys Ile Trp Glu Asn Leu Pro Glu Ala Gly Lys Thr Ile
    135                 140                 145

aaa ctg gca cat aaa atc aat gcg tat gac ctg ctg ccg aag aaa aaa      576
Lys Leu Ala His Lys Ile Asn Ala Tyr Asp Leu Leu Pro Lys Lys Lys
150                 155                 160                 165

aaa tat tat aga tat agc ggc agc ctg aca aca ccg cct tgc agc gaa      624
Lys Tyr Tyr Arg Tyr Ser Gly Ser Leu Thr Thr Pro Pro Cys Ser Glu
                170                 175                 180

ggc gtt aga tgg att gtt atg gaa gaa gaa atg gaa ctg agc aaa gaa      672
Gly Val Arg Trp Ile Val Met Glu Glu Glu Met Glu Leu Ser Lys Glu
            185                 190                 195

caa atc gaa aaa ttt cgc aaa ctg atg gga ggc gat aca aat aga ccg      720
Gln Ile Glu Lys Phe Arg Lys Leu Met Gly Gly Asp Thr Asn Arg Pro
        200                 205                 210
```

```
gtt caa ccg ctg aat gca aga atg att atg gaa atg gat taa             762
Val Gln Pro Leu Asn Ala Arg Met Ile Met Glu Met Asp
    215                 220                 225


<210> SEQ ID NO 4
<211> LENGTH: 253
<212> TYPE: PRT
<213> ORGANISM: Artificial
<220> FEATURE:
<223> OTHER INFORMATION: Synthetic Construct

<400> SEQUENCE: 4

Met Lys Lys Pro Leu Gly Lys Ile Val Ala Ser Thr Ala Leu Leu Ile
        -25                 -20                 -15

Ser Val Ala Phe Ser Ser Ser Ile Ala Ser Ala Gly Gly Val Gly His
    -10                 -5              -1  1               5

Trp Ser Tyr His Gly Glu Thr Gly Pro Gln His Trp Gly Asp Leu Lys
                10                  15                  20

Asn Glu Tyr Ile Met Cys Lys Ile Gly Lys Asn Gln Ser Pro Val Asp
            25                  30                  35

Ile Ser Arg Ile Val Glu Ala Glu Leu Glu Lys Ile Lys Ile Asn Tyr
        40                  45                  50

Ser Ser Gly Gly Ser Ser Ile Thr Asn Asn Gly His Thr Ile Lys Val
    55                  60                  65

Ser Tyr Glu Pro Gly Ser Tyr Ile Ile Val Asp Gly Ile Arg Phe Glu
70                  75                  80                  85

Leu Lys Gln Phe His Phe His Ala Pro Ser Glu His Thr Ile Lys Gly
                90                  95                  100

Lys Ser Tyr Pro Phe Glu Ala His Phe Val His Ala Asp Lys Asp Gly
            105                 110                 115

Asn Leu Ala Val Ile Gly Val Ile Phe Lys Glu Gly Lys Lys Asn Pro
        120                 125                 130

Ile Ile Glu Lys Ile Trp Glu Asn Leu Pro Glu Ala Gly Lys Thr Ile
    135                 140                 145

Lys Leu Ala His Lys Ile Asn Ala Tyr Asp Leu Leu Pro Lys Lys Lys
150                 155                 160                 165

Lys Tyr Tyr Arg Tyr Ser Gly Ser Leu Thr Thr Pro Pro Cys Ser Glu
                170                 175                 180

Gly Val Arg Trp Ile Val Met Glu Glu Glu Met Glu Leu Ser Lys Glu
            185                 190                 195

Gln Ile Glu Lys Phe Arg Lys Leu Met Gly Gly Asp Thr Asn Arg Pro
        200                 205                 210

Val Gln Pro Leu Asn Ala Arg Met Ile Met Glu Met Asp
    215                 220                 225


<210> SEQ ID NO 5
<211> LENGTH: 226
<212> TYPE: PRT
<213> ORGANISM: Artificial
<220> FEATURE:
<223> OTHER INFORMATION: Mature Logatchev CA sequence

<400> SEQUENCE: 5

Gly Gly Val Gly His Trp Ser Tyr His Gly Glu Thr Gly Pro Gln His
1               5                   10                  15

Trp Gly Asp Leu Lys Asn Glu Tyr Ile Met Cys Lys Ile Gly Lys Asn
            20                  25                  30
```

-continued

```
Gln Ser Pro Val Asp Ile Ser Arg Ile Val Glu Ala Glu Leu Glu Lys
        35                  40                  45

Ile Lys Ile Asn Tyr Ser Ser Gly Gly Ser Ser Ile Thr Asn Asn Gly
    50                  55                  60

His Thr Ile Lys Val Ser Tyr Glu Pro Gly Ser Tyr Ile Ile Val Asp
65                  70                  75                  80

Gly Ile Arg Phe Glu Leu Lys Gln Phe His Phe His Ala Pro Ser Glu
                85                  90                  95

His Thr Ile Lys Gly Lys Ser Tyr Pro Phe Glu Ala His Phe Val His
            100                 105                 110

Ala Asp Lys Asp Gly Asn Leu Ala Val Ile Gly Val Ile Phe Lys Glu
        115                 120                 125

Gly Lys Lys Asn Pro Ile Ile Glu Lys Ile Trp Glu Asn Leu Pro Glu
    130                 135                 140

Ala Gly Lys Thr Ile Lys Leu Ala His Lys Ile Asn Ala Tyr Asp Leu
145                 150                 155                 160

Leu Pro Lys Lys Lys Lys Tyr Tyr Arg Tyr Ser Gly Ser Leu Thr Thr
                165                 170                 175

Pro Pro Cys Ser Glu Gly Val Arg Trp Ile Val Met Glu Glu Glu Met
            180                 185                 190

Glu Leu Ser Lys Glu Gln Ile Glu Lys Phe Arg Lys Leu Met Gly Gly
        195                 200                 205

Asp Thr Asn Arg Pro Val Gln Pro Leu Asn Ala Arg Met Ile Met Glu
    210                 215                 220

Met Asp
225


<210> SEQ ID NO 6
<211> LENGTH: 226
<212> TYPE: PRT
<213> ORGANISM: Artificial
<220> FEATURE:
<223> OTHER INFORMATION: Logatchev CA variant with I99V mutation

<400> SEQUENCE: 6

Gly Gly Val Gly His Trp Ser Tyr His Gly Glu Thr Gly Pro Gln His
1               5                   10                  15

Trp Gly Asp Leu Lys Asn Glu Tyr Ile Met Cys Lys Ile Gly Lys Asn
            20                  25                  30

Gln Ser Pro Val Asp Ile Ser Arg Ile Val Glu Ala Glu Leu Glu Lys
        35                  40                  45

Ile Lys Ile Asn Tyr Ser Ser Gly Gly Ser Ser Ile Thr Asn Asn Gly
    50                  55                  60

His Thr Ile Lys Val Ser Tyr Glu Pro Gly Ser Tyr Ile Ile Val Asp
65                  70                  75                  80

Gly Ile Arg Phe Glu Leu Lys Gln Phe His Phe His Ala Pro Ser Glu
                85                  90                  95

His Thr Val Lys Gly Lys Ser Tyr Pro Phe Glu Ala His Phe Val His
            100                 105                 110

Ala Asp Lys Asp Gly Asn Leu Ala Val Ile Gly Val Ile Phe Lys Glu
        115                 120                 125

Gly Lys Lys Asn Pro Ile Ile Glu Lys Ile Trp Glu Asn Leu Pro Glu
    130                 135                 140

Ala Gly Lys Thr Ile Lys Leu Ala His Lys Ile Asn Ala Tyr Asp Leu
145                 150                 155                 160
```

Leu Pro Lys Lys Lys Lys Tyr Tyr Arg Tyr Ser Gly Ser Leu Thr Thr
165 170 175

Pro Pro Cys Ser Glu Gly Val Arg Trp Ile Val Met Glu Glu Glu Met
180 185 190

Glu Leu Ser Lys Glu Gln Ile Glu Lys Phe Arg Lys Leu Met Gly Gly
195 200 205

Asp Thr Asn Arg Pro Val Gln Pro Leu Asn Ala Arg Met Ile Met Glu
210 215 220

Met Asp
225

<210> SEQ ID NO 7
<211> LENGTH: 226
<212> TYPE: PRT
<213> ORGANISM: Artificial
<220> FEATURE:
<223> OTHER INFORMATION: Logatchev CA variant with R40S+I99V mutation

<400> SEQUENCE: 7

Gly Gly Val Gly His Trp Ser Tyr His Gly Glu Thr Gly Pro Gln His
1 5 10 15

Trp Gly Asp Leu Lys Asn Glu Tyr Ile Met Cys Lys Ile Gly Lys Asn
20 25 30

Gln Ser Pro Val Asp Ile Ser Ser Ile Val Glu Ala Glu Leu Glu Lys
35 40 45

Ile Lys Ile Asn Tyr Ser Ser Gly Gly Ser Ser Ile Thr Asn Asn Gly
50 55 60

His Thr Ile Lys Val Ser Tyr Glu Pro Gly Ser Tyr Ile Ile Val Asp
65 70 75 80

Gly Ile Arg Phe Glu Leu Lys Gln Phe His Phe His Ala Pro Ser Glu
85 90 95

His Thr Val Lys Gly Lys Ser Tyr Pro Phe Glu Ala His Phe Val His
100 105 110

Ala Asp Lys Asp Gly Asn Leu Ala Val Ile Gly Val Ile Phe Lys Glu
115 120 125

Gly Lys Lys Asn Pro Ile Ile Glu Lys Ile Trp Glu Asn Leu Pro Glu
130 135 140

Ala Gly Lys Thr Ile Lys Leu Ala His Lys Ile Asn Ala Tyr Asp Leu
145 150 155 160

Leu Pro Lys Lys Lys Lys Tyr Tyr Arg Tyr Ser Gly Ser Leu Thr Thr
165 170 175

Pro Pro Cys Ser Glu Gly Val Arg Trp Ile Val Met Glu Glu Glu Met
180 185 190

Glu Leu Ser Lys Glu Gln Ile Glu Lys Phe Arg Lys Leu Met Gly Gly
195 200 205

Asp Thr Asn Arg Pro Val Gln Pro Leu Asn Ala Arg Met Ile Met Glu
210 215 220

Met Asp
225

<210> SEQ ID NO 8
<211> LENGTH: 226
<212> TYPE: PRT
<213> ORGANISM: Artificial
<220> FEATURE:
<223> OTHER INFORMATION: Logatchev CA variant with R40S+G56L+I99V
mutation

<400> SEQUENCE: 8

Gly Gly Val Gly His Trp Ser Tyr His Gly Glu Thr Gly Pro Gln His
1 5 10 15

Trp Gly Asp Leu Lys Asn Glu Tyr Ile Met Cys Lys Ile Gly Lys Asn
20 25 30

Gln Ser Pro Val Asp Ile Ser Ser Ile Val Glu Ala Glu Leu Glu Lys
35 40 45

Ile Lys Ile Asn Tyr Ser Ser Leu Gly Ser Ser Ile Thr Asn Asn Gly
50 55 60

His Thr Ile Lys Val Ser Tyr Glu Pro Gly Ser Tyr Ile Ile Val Asp
65 70 75 80

Gly Ile Arg Phe Glu Leu Lys Gln Phe His Phe His Ala Pro Ser Glu
85 90 95

His Thr Val Lys Gly Lys Ser Tyr Pro Phe Glu Ala His Phe Val His
100 105 110

Ala Asp Lys Asp Gly Asn Leu Ala Val Ile Gly Val Ile Phe Lys Glu
115 120 125

Gly Lys Lys Asn Pro Ile Ile Glu Lys Ile Trp Glu Asn Leu Pro Glu
130 135 140

Ala Gly Lys Thr Ile Lys Leu Ala His Lys Ile Asn Ala Tyr Asp Leu
145 150 155 160

Leu Pro Lys Lys Lys Lys Tyr Tyr Arg Tyr Ser Gly Ser Leu Thr Thr
165 170 175

Pro Pro Cys Ser Glu Gly Val Arg Trp Ile Val Met Glu Glu Glu Met
180 185 190

Glu Leu Ser Lys Glu Gln Ile Glu Lys Phe Arg Lys Leu Met Gly Gly
195 200 205

Asp Thr Asn Arg Pro Val Gln Pro Leu Asn Ala Arg Met Ile Met Glu
210 215 220

Met Asp
225

<210> SEQ ID NO 9
<211> LENGTH: 226
<212> TYPE: PRT
<213> ORGANISM: Artificial
<220> FEATURE:
<223> OTHER INFORMATION: Logatchev CA variant with D19F+K21R+R40S+G56L+ I99V mutation

<400> SEQUENCE: 9

Gly Gly Val Gly His Trp Ser Tyr His Gly Glu Thr Gly Pro Gln His
1 5 10 15

Trp Gly Phe Leu Arg Asn Glu Tyr Ile Met Cys Lys Ile Gly Lys Asn
20 25 30

Gln Ser Pro Val Asp Ile Ser Ser Ile Val Glu Ala Glu Leu Glu Lys
35 40 45

Ile Lys Ile Asn Tyr Ser Ser Leu Gly Ser Ser Ile Thr Asn Asn Gly
50 55 60

His Thr Ile Lys Val Ser Tyr Glu Pro Gly Ser Tyr Ile Ile Val Asp
65 70 75 80

Gly Ile Arg Phe Glu Leu Lys Gln Phe His Phe His Ala Pro Ser Glu
85 90 95

His Thr Val Lys Gly Lys Ser Tyr Pro Phe Glu Ala His Phe Val His
100 105 110

-continued

```
Ala Asp Lys Asp Gly Asn Leu Ala Val Ile Gly Val Ile Phe Lys Glu
        115                 120                 125

Gly Lys Lys Asn Pro Ile Ile Glu Lys Ile Trp Glu Asn Leu Pro Glu
    130                 135                 140

Ala Gly Lys Thr Ile Lys Leu Ala His Lys Ile Asn Ala Tyr Asp Leu
145                 150                 155                 160

Leu Pro Lys Lys Lys Lys Tyr Tyr Arg Tyr Ser Gly Ser Leu Thr Thr
                165                 170                 175

Pro Pro Cys Ser Glu Gly Val Arg Trp Ile Val Met Glu Glu Glu Met
            180                 185                 190

Glu Leu Ser Lys Glu Gln Ile Glu Lys Phe Arg Lys Leu Met Gly Gly
        195                 200                 205

Asp Thr Asn Arg Pro Val Gln Pro Leu Asn Ala Arg Met Ile Met Glu
    210                 215                 220

Met Asp
225
```

HEAT-STABLE METAGENOMIC CARBONIC ANHYDRASES AND THEIR USE

CROSS-REFERENCE TO RELATED APPLICATIONS

This application is a 35 U.S.C. 371 national application of PCT/US2017/042994 filed Jul. 20, 2017, which claims priority from European patent application no. 16180365.5 filed Jul. 20, 2016. The contents of these applications are fully incorporated herein by reference.

REFERENCE TO A SEQUENCE LISTING

This application contains a Sequence Listing in computer readable form, which is incorporated herein by reference.

FIELD OF THE INVENTION

The present invention relates to polypeptides, identified as a metagenomic sequence isolated from the Logatchev hydrothermal vent, having carbonic anhydrase activity and catalytic domains, and polynucleotides encoding the polypeptides and catalytic domains. The invention also relates to nucleic acid constructs, vectors, and host cells comprising the polynucleotides as well as methods of producing and using the polypeptides and catalytic domains.

BACKGROUND

Carbonic anhydrase (CA) selectively and reversibly catalyzes the reaction of carbon dioxide with water to produce bicarbonate (Reaction 1) with high catalytic efficiency:

$$CO_2+H_2O \leftrightarrow HCO_3^-+H^+$$

This catalytic activity can facilitate the separation of $CO_2$ from gas mixtures, can facilitate the conversion of $CO_2$ to alternative chemical forms, such as bicarbonate and carbonate, and can facilitate the release of $CO_2$ from compositions comprising bicarbonate, especially aqueous compositions. Carbonic anhydrases (EC 4.2.1.1) are abundant in nature and found in all domains of life. However, many CAs lack the thermal and physical stability to withstand commercial applications.

Carbonic anhydrases are encoded by several distinct gene families, including the three families (or classes) called α-CAs, β-CAs, and γ-CAs (C. T. Supuran, A. Scozzafava, and J. Conway, Eds., *Carbonic anhydrase; its inhibitors and activators,* 2004, Boca Raton: CRC Press LLC; Hewett-Emmett and Tashian, 1996, *Mol. Phylogenet. Evol.* 5: 50-77). Other classes of CAs have been found only in certain organisms, such as diatoms (Xu et al., 2008, Structure and metal exchange in the cadmium carbonic anhydrase of marine diatoms, *Nature* 542: 56-61). The different CA families have very low protein sequence similarity and differ in their three-dimensional structures. Also, there can be structural variation within a CA-family. For example, α-CAs can exist as monomers containing only a single protein chain, or can exist as multimers, such as dimers or tetramers, in which more than one protein chain monomers are bound to one another by covalent or ionic bonds or by physical association, such as hydrophobic interaction, or a combination of these (James et al., 2014, The structure of a tetrameric α-carbonic anhydrase from *Thermovibrio ammonificans* reveals a core formed around intermolecular disulfides that contribute to its thermostability, *Acta Cryst. D*70: 2607-2618). Regardless of these sequence and structural differences, the active sites of different carbonic anhydrases typically contain a catalytically essential Zn(II) ion that binds water to form a Zn-hydroxide nucleophile when the water molecule is deprotonated in the catalytically active form of the enzyme (Christianson and Fierke, 1996, *Acc. Chem. Res.* 29: 331-339). In α-CAs, the active-site zinc is held in place by three histidine residues.

An individual organism can have several different CAs located in different regions of the cell or tissues, or secreted outside the cell. CAs participate in a variety of metabolic functions, such as respiration and pH control, provision of bicarbonate for fatty acid and Krebs cycle biosynthesis reactions (Nishimori et al., 2007, Carbonic anhydrase inhibitors: the inhibition profiles of the human mitochondrial isoforms VA and VB with anions are very different, *Bioorg. Med. Chem.* 15: 6742-6747), and participate in the carbon concentrating mechanism for photosynthetic carbon fixation (Pena et al., 2010, Structural basis of the oxidative activation of the carboxysomal gamma-carbonic anhydrase, CcmM, *PNAS* 107: 2455-60). Using genetic and biological engineering techniques, the substitution of indigenous CAs with CAs from different sources can improve these biological processes.

CAs catalyze a variety of different chemical reactions (C. T. Supuran, A. Scozzafava, and J. Conway, Eds., *Carbonic anhydrase: its inhibitors and activators,* 2004, Boca Raton: CRC Press LLC), including ester hydrolysis. The reaction of most widespread interest is the CA-catalyzed inter-conversion between carbon dioxide and bicarbonate. This reaction is important for physiological and medical interests, as well has become increasingly important in the field of industrial $CO_2$ gas separation and sequestration. CAs are especially of interest as efficient, environmentally-benign catalysts for use in $CO_2$ capture processes to help prevent $CO_2$ emissions to the atmosphere. In order to meet the techno-economic requirements for industrial applications, CAs must remain active and physically stable under industrially-relevant application conditions for extended periods of time while exposed to harsh environments that may include high temperature, high salt concentrations, and concentrated chemical solutions. For example, $CO_2$ separation systems and processes commonly utilize high concentration alkaline solutions and solutions with high ionic strength to function as $CO_2$ absorption media.

Furthermore, CA thermostability enables the use of heat treatment as a purification process for isolating CA from other proteins and contaminants during CA production processes. Also, thermostability extends the storage stability of CA products during manufacture, use, or during idle periods, for example storage in a hot warehouse. For some applications, CA may have to withstand repeated exposure to lower and higher temperatures during use.

Consequently, there is a need for heat-stable CAs that can maintain enzyme activity for extended periods of time when exposed to harsh operational environments.

SUMMARY OF THE INVENTION

The present invention provides polypeptides having carbonic anhydrase activity and polynucleotides encoding the polypeptides.

Accordingly, the present invention relates to polypeptides having carbonic anhydrase activity, which has at least 80% sequence identity to the mature polypeptide of SEQ ID NO: 2, or a fragment thereof that has carbonic anhydrase activity.

The present invention also relates to polynucleotides encoding the polypeptides of the present invention; nucleic acid constructs; recombinant expression vectors; recombinant host cells comprising the polynucleotides; and methods of producing the polypeptides.

The present invention also relates to methods and uses of the polypeptides having carbonic anhydrase activity as catalysts for the absorption of carbon dioxide by media comprising water, or release of carbon dioxide from media comprising water, and relates to reactors and systems for separating carbon dioxide and compositions useful for such separation processes.

The present invention also relates to nucleic acid constructs, expression vectors, and recombinant host cells comprising the polynucleotides; and methods of producing the polypeptides having carbonic anhydrase activity.

Other aspects and embodiments of the invention will be apparent from the description and examples.

DEFINITIONS

Figure 1:
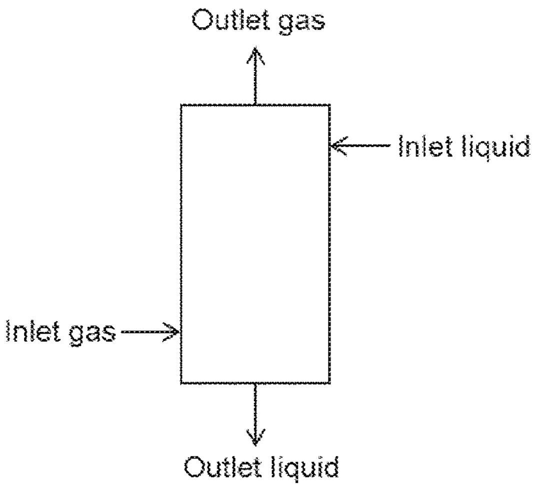
FIG. 1 shows a schematic diagram of a counter-current gas-liquid contactor. In a typical counter-current gas-liquid contactor, the $CO_2$-rich inlet gas (e.g., a mixed gas comprising $CO_2$) enters the bottom of the contactor and travels upwards, while the $CO_2$-lean inlet liquid enters the top of the contactor and flows downwards. The liquid flow can be in the form of droplets, such as a spray, or as a continuous stream or sheet of liquid, such as flows along a surface, or a combination of these. Inside the gas-liquid contactor, $CO_2$ from the $CO_2$-rich inlet gas is absorbed by the liquid and carried out from the contactor as a $CO_2$-rich outlet liquid. $CO_2$-rich liquid means the liquid comprises an increased amount of $CO_2$ in its dissolved gaseous form or any ionic form of $CO_2$, such as bicarbonate, or a reaction product of $CO_2$ and a compound in the inlet absorption liquid, relative to the $CO_2$-lean liquid. $CO_2$-lean gas, from which $CO_2$ has been partially or completely removed, exits the contactor as the outlet gas. A counter-current gas-liquid contactor is the most common type of gas-liquid contactor used industrially. The internals of the contactor can be largely empty with liquid sprayed down from the top and gas flowing up from the bottom, or, more commonly, the contactor contains different types of packing materials to increase the residence time of gas and liquid inside the contactor and promote a large surface area of interaction between the gas and liquid. The liquid is typically delivered onto the packing materials from spray nozzles or other types of openings designed to deliver the liquid in a uniform fashion over the packing material. The liquid is comprised of absorption compounds, water, and other components that may be needed to optimize the process. For example, the liquid can comprise CA in soluble form or as small particles of suspended biocatalyst that flow through the contactor. The packing material may be coated with or have CA attached to it.
Figure 2:
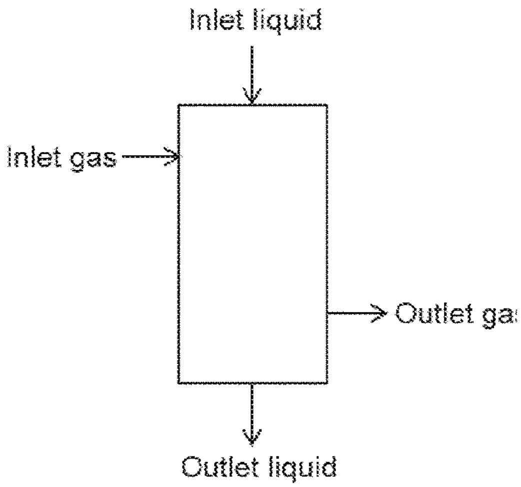
FIG. 2 shows a schematic diagram of a co-current gas-liquid contactor. In a typical co-current gas-liquid contactor, the $CO_2$-rich inlet gas and $CO_2$-lean inlet liquid enter the contactor at the same end (e.g., the top) and exit at the same end. The outlet gas preferably exits the contactor at a location above any sump present for collection of the outlet liquid. This type of contactor can provide a lower pressure drop compared to a counter-current contactor, because the gas and liquid flows are both moving in the same direction, however the efficiency of gas-liquid interaction may be lower compared to a counter-current design. The internals and function of the co-current contactor are as described for FIG. 1, with the exception that the gas and liquid are flowing in the same direction.
Figure 3:
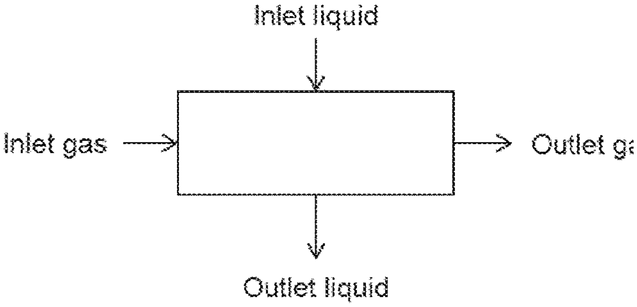
FIG. 3 shows a schematic diagram of a perpendicular-flow gas-liquid contactor. In a perpendicular gas-liquid contactor, the gas typically travels in an overall horizontal direction from the inlet gas to the outlet gas while the liquid overall travels vertically, from inlet liquid at the top to outlet liquid at the bottom to take advantage of gravity. This contactor design can take advantage of specialized liquid delivery systems, such as those generating flat sheets of liquid, to create high gas-liquid contact in a compact design that does not require tall vertical structures. The contactor can have internal baffles or packing materials to enhance gas-liquid contact and control gas and liquid flows. The internals and function of the co-current contactor are as described for FIG. 1, with the exception that the overall gas and liquid flows are perpendicular to each other.
Figure 4:
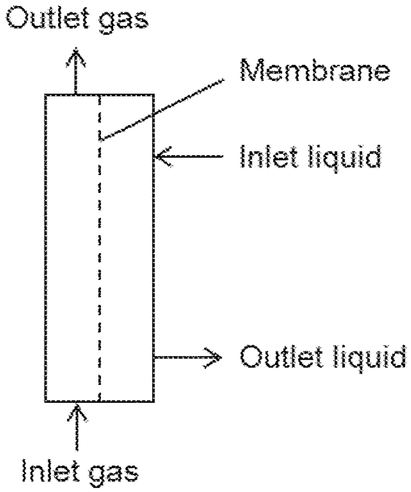
FIG. 4 shows a schematic diagram of a membrane gas-liquid contactor. A membrane contactor utilizes a gas permeable membrane (dotted line) to separate the gas flow from the liquid flow. The diagram shows counter-current flow of gas and liquid, though co-current and perpendicular-type flows are also possible. The $CO_2$-rich inlet gas comes in contact with the membrane and $CO_2$, preferably selectively, passes across the membrane into the $CO_2$ absorption liquid. Membranes used in these contactors can be microporous, allowing the surface of the liquid to be exposed to the gas through pores in the membrane that are small enough to prevent the liquid from passing through due to physical phenomena, such as surface tension. Alternatively, the membranes can be non-porous, yet made from $CO_2$-gas permeable materials. Microporous membranes may provide faster $CO_2$ absorption rates, while non-porous membranes may minimize liquid losses to evaporation in the gas stream. While passing through the contactor, the inlet liquid becomes enriched in $CO_2$, such that the outlet liquid is $CO_2$-rich by comparison, and the inlet gas becomes depleted in $CO_2$, such that the outlet gas is $CO_2$-lean. The diagram only shows a representation of the basic functional unit of a membrane contactor, which in operational form contains many layers of stacked membranes or bundles of tubular, or hollow-fiber, membranes arranged in suitable housing with dividers and control mechanisms to optimally direct the gas and liquid flows. Membrane contactors are used for large industrial gas scrubbing applications as well as for small units, such as for $CO_2$ removal during dialysis in which the semi-permeable membrane may separate two liquids, such as $CO_2$-rich blood and a $CO_2$-lean buffer solution capable of absorbing excess $CO_2$ from the blood. CA can be present in soluble or suspended particulate form in the liquid and can be immobilized on or in the membrane.
Figure 5:
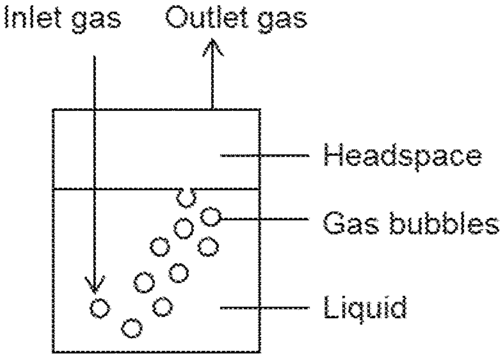
FIG. 5 shows a schematic diagram of a bubble-tank gas-liquid contactor. The system shown is a batch-mode bubble-tank gas-liquid contactor, in which a stream of inlet gas comprising $CO_2$ is bubbled (or sparged) through a fixed amount of absorption liquid. $CO_2$ is absorbed into the liquid such that the outlet gas is depleted in $CO_2$ compared to the inlet gas. In batch mode, eventually the liquid will reach a maximum $CO_2$ absorption capacity, and the $CO_2$-rich inlet gas can be directed to another batch reactor containing $CO_2$-lean absorption liquid, or the batch reactor can be emptied and filled with fresh $CO_2$-lean absorption liquid, or the inlet gas flow can be stopped while the batch reactor is changed from absorption mode to $CO_2$ desorption mode, such as by applying heat, sweep gas or vacuum to the batch reactor, to release absorbed $CO_2$ from the $CO_2$-rich liquid. This type of contactor can, for example, be used for producing solid precipitated forms of $CO_2$, such as carbonates, like calcium, magnesium, and manganese carbonate. Gas delivery nozzles that produce very small gas bubbles can enhance the gas-liquid contact and improve $CO_2$ absorption efficiency. A bubble-tank contactor can be enclosed equipment or can operate in open environments, such as bubbling $CO_2$-rich gas streams into algae ponds. CA can be present in soluble or suspended particulate form in the liquid and can be immobilized on the surfaces of structures or packing immersed in or exposed to the liquid.
Figure 6:
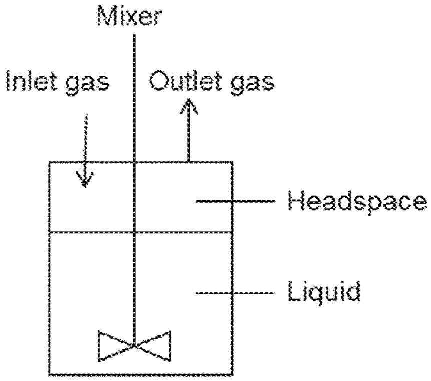
FIG. 6 shows a schematic diagram of a batch-mode stirred-tank gas-liquid contactor. In this type of contactor the $CO_2$-rich gas is exposed to the surface of a liquid leading to $CO_2$ gas absorption into the liquid. The liquid may be quiescent or may be mixed by some means to cause movement of the liquid and liquid components. The principle of a stirred-tank contactor can apply to controlled enclosed equipment or can apply to open environments, such the absorption of $CO_2$ from air into a body of water, like an ocean. CA can be present in soluble or suspended particulate form in the liquid and can be immobilized on the surfaces of structures, mixers or packing immersed in or exposed to the liquid.

Carbonic anhydrase: The term “carbonic anhydrase activity” or “CA activity” is defined herein as an EC 4.2.1.1 activity which catalyzes the conversion between carbon dioxide and bicarbonate: $CO_2+H_2O \leftrightarrow HCO^-_3+H^+$.

For purposes of the present invention, CA activity is determined according to the procedure described in Example 3. The polypeptides of the present invention are considered to have CA activity if they have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the CA activity of the polypeptide consisting of the amino acid sequence corresponding to amino acid residues 1 to 226 of SEQ ID NO: 2.

Allelic variant: The term “allelic variant” means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term “catalytic domain” means the region of an enzyme containing the catalytic machinery of the enzyme.

cDNA: The term “cDNA” means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term “coding sequence” means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has carbonic anhydrase activity. In one aspect, a fragment contains at least 220 amino acid residues (e.g., amino acids 1 to 220 of SEQ ID NO: 2), at least 210 amino acid residues (e.g., amino acids 1 to 210 of SEQ ID NO: 2), or at least 200 amino acid residues (e.g., amino acids 1 to 200 of SEQ ID NO: 2).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g., a host cell may be genetically modified to express the polypeptide of the invention. The fermentation broth from that host cell will comprise the isolated polypeptide.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 226 of SEQ ID NO: 2. Amino acids −18 to −1 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. In one aspect, a mature polypeptides contains up to 230 amino acid residues, up to 235 amino acid residues, or up to 240 amino acid residues.

Mature polypeptide coding sequence: The term "mature polypeptide coding sequence" means a polynucleotide that encodes a mature polypeptide having carbonic anhydrase activity. In one aspect, the mature polypeptide coding sequence is nucleotides 55 to 735 of SEQ ID NO: 1, and nucleotides 1 to 54 of SEQ ID NO: 1 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et at, 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxy ribonucleotides×100)/(Length of Alignment−Total Number of Gaps in Alignment)

Stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having carbonic anhydrase activity. In one aspect, a subsequence contains at least 660 nucleotides (e.g., nucleotides 55 to 714 of SEQ ID NO: 1), at least 630 nucleotides (e.g., nucleotides 55 to 684 of SEQ ID NO: 1), or at least 600 nucleotides (e.g., nucleotides 55 to 654 of SEQ ID NO: 1).

Variant: The term "variant" means a polypeptide having carbonic anhydrase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

DETAILED DESCRIPTION OF THE INVENTION

The carbonic anhydrase shown as the mat re amino acid sequence of SEQ ID NO: 2 (which is hereinafter also referred to as 'Logatchev CA') was identified as a metagenomic sequence isolated from the Logatchev hydrothermal vent (Perner et al., 2013, *Environ. Microbiol.* 15: 1551-1560). Use of the metagenomics sequencing technique resulted in the discovery of a new diversity of thermostable carbonic anhydrases not previously found by other methods. Traditional microbial genome sequencing and genomics rely upon cultivated clonal cultures isolated from environmental samples. However, studies of 16S ribosomal RNA in environmental samples have revealed that cultivation-based methods find less than 1% of the bacterial and archaeal species in a sample.

Polypeptides Having Carbonic Anhydrase Activity

In an embodiment, the present invention relates to polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have carbonic anhydrase activity. In one aspect, the polypeptides differ by up to 10 amino acids, e.g., 1, 2, 3, 4, 5, 6, 7, 8, 9, or 10, from the mature polypeptide of SEQ ID NO: 2.

In a particular embodiment the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the carbonic anhydrase activity of the mature polypeptide of SEQ ID NO: 2.

In a particular embodiment the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the carbonic anhydrase activity of the mature polypeptide of SEQ ID NO: 2. In a particular embodiment the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the carbonic anhydrase activity of the mature polypeptide of SEQ ID NO: 2. In a particular embodiment the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the carbonic anhydrase activity of the mature polypeptide of SEQ ID NO: 2.

In a particular embodiment the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the carbonic anhydrase activity of the mature polypeptide of SEQ ID NO: 2.

In a particular embodiment the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the carbonic anhydrase activity of the mature polypeptide of SEQ ID NO: 2.

In a particular embodiment the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the carbonic anhydrase activity of the mature polypeptide of SEQ ID NO: 2.

In an embodiment, the polypeptide has been isolated. A polypeptide of the present invention preferably comprises or consists of the amino acid sequence of SEQ ID NO: 2 or an allelic variant thereof; or is a fragment thereof having carbonic anhydrase activity. In another aspect, the polypeptide comprises or consists of the mature polypeptide of SEQ ID NO: 2. In another aspect, the polypeptide comprises or consists of amino acids 1 to 226 of SEQ ID NO: 2.

In another embodiment, the present invention relates to a polypeptide having carbonic anhydrase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complement of (i) (Sambrook et al., 1989, *Molecular Cloning, A Laboratory Manual,* 2d edition, Cold Spring Harbor, N.Y.). In an embodiment, the polypeptide has been isolated.

The polynucleotide of SEQ ID NO: 1 or a subsequence thereof, as well as the polypeptide of SEQ ID NO: 2 or a fragment thereof may be used to design nucleic acid probes to identify and clone DNA encoding polypeptides having carbonic anhydrase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having carbonic anhydrase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under low to very high stringency conditions. Molecules to which the nucleic acid probe hybridizes under these conditions can be detected using, for example, X-ray film or any other detection means known in the art.

In one aspect, the nucleic acid probe is nucleotides 1 to 50, nucleotides 50 to 100, nucleotides 100 to 150, or nucleotides 150 to 200 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In another embodiment, the present invention relates to a polypeptide having carbonic anhydrase activity encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered.

The carbonic anhydrase polypeptides of the invention may have, and be identified by, the consensus sequence motif: S-E-[HN]-x-[LIVM]-x(4)-[FYH]-x(2)-E-[LIVMGA]-H-[LIVMFA](2). The respective consensus residues corresponds to positions 113 to 129 in SEQ ID NO: 2. In a preferred embodiment all consensus positions are present in the carbonic anhydrase.

The amino acid residues H108, H110, and H127 of SEQ ID NO: 2 form a histidine triad which is important for catalysis. In a preferred embodiment of the present invention the carbonic anhydrase contains a histidine in an amino acid position corresponding to position 108, 110, and 127 of SEQ ID NO: 2.

The amino acid residues H83, E114, Q106 and T193 of SEQ ID NO: 2 participate in a proton shuttle mechanism, which also is relevant for the catalytic activity of the enzyme. In a further embodiment the carbonic anhydrase contains a histidine in an amino acid position corresponding to position 83 of SEQ ID NO: 2, and/or a glutamine in an amino acid position corresponding to position 106 of SEQ ID NO: 2, and/or a glutamic acid in an amino acid position corresponding to position 114 of SEQ ID NO: 2, and/or a threonine in an amino acid position corresponding to position 193 of SEQ ID NO: 2. Preferably, at least one of the proton shuttle positions are present, more preferably at least two proton shuttle positions are present, more preferably at least three proton shuttle positions are present, and most preferably all the proton shuttle positions are present in the carbonic anhydrase of the invention.

The amino acid residues C45 and C197 of SEQ ID NO: 2 engage in a cysteine bridge and may therefore be important for the stability of the carbonic anhydrase. In a preferred embodiment of the present invention the carbonic anhydrase contains a cysteine in an amino acid position corresponding to position 45 and 197 of SEQ ID NO: 2.

Other essential amino acids can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for carbonic anhydrase activity to identify amino acid residues that are critical to the activity of the molecule. See also, Hilton et al., 1996, *J. Bid. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Md. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone FOR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

As shown in the Examples, the carbonic anhydrases of the invention may include one or more substitutions in position(s) corresponding to D19, K21, R40, G56, or I99 of SEQ ID NO: 2. Such substitutions may be selected from the group consisting of D19F, K21R, R40S, G56L, and 199V.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBOJ.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al, 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

Sources of Polypeptides Having Carbonic Anhydrase Activity

A polypeptide having carbonic anhydrase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

The technique of metagenomics sequencing is an alternative technique that overcomes the difficulties of cultivating specific organisms by probing the genetic composition of a pool of one or more organisms, often pools of many organisms, for gene sequences and/or genetic fragments without the need for cultivation. The technique of metagenomics sequencing enables identification of CA gene sequences originating from uncultivated and unclassified organisms, and can also result in the creation of non-natural synthetic constructs through selection of overlapping polynucleotide fragments from a genetic mixture to produce novel polynucleotides encoding for polypeptides with CA activity.

Polynucleotides

The present invention also relates to polynucleotides encoding a polypeptide or a catalytic domain, as described herein. In an embodiment, the polynucleotide encoding the polypeptide or catalytic domain of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application, Academic Press*, New York. Other nucleic acid amplification procedures such as ligase chain reaction (LCR), ligation activated transcription (LAT) and polynucleotide-based amplification (NASBA) may be used.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, Molecular Microbiology 13: 97-107), *E. coli* lac operon, *E. coli* trc promoter (Egon et al., 1988, Gene 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* those phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* those phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* those phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* those phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* those phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprf), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated.

Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sam brook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylo-*

*bacter, E. coli, Flavobacterium, Fusobacterium, Helicobacter, Ilyobacter, Neisseria, Pseudomonas, Salmonella*, and *Ureaplasma.*

The bacterial host cell may be any *Bacillus* cell including, but not limited to, *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, Mol. Gen. Genet. 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DMA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the *Fungi Imperfecti* (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kiuyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus* nigeL *Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known perse. Suitable procedures for transformation of *Aspergillus* and *Trichoderma* host cells are described in EP 238023, Yelton et al., 1984, *Proc. Nati. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and*

*Molecular Biology, Methods in Enzymology*, Volume 194, pp 182-187, Academic Press, Inc., New York; I to et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermenters in a suitable medium and under conditions allowing the polypeptide to be expressed and/or isolated. The cultivation takes place in a suitable nutrient medium comprising carbon and nitrogen sources and inorganic salts, using procedures known in the art. In particular, inorganic salts of zinc, such as zinc chloride ($ZnCl_2$), zinc sulfate ($ZnSO_4$), and the like, can be added. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Jansen and Ryden, editors, VCH Publishers, New York, 1989) to obtain substantially pure polypeptides. Inorganic salts of zinc, such as zinc chloride ($ZnCl_2$), zinc sulfate ($ZnSO_4$), and the like, can be added during enzyme production, during recovery processes or after enzyme production, as needed, to ensure sufficient Zn(II) is present in the enzyme active site for optimal catalytic activity.

In an alternative aspect, the polypeptide is not recovered, but rather a host cell of the present invention expressing the polypeptide is used as a source of the polypeptide.

Production in Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in such a polypeptide. The term "enriched" indicates that the carbonic anhydrase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carbonic anhydrase, carboxypeptidase, catalase, cellobiohydrolase, cellulase, chitinase, cutinase, cyclodextrin glycosyltransferase, decarboxylase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In a particular embodiment the metagenomic Logatchev CA of the invention is the major (polypeptide) component of the composition, e.g., a mono-component composition. In a mono-component composition the Logatchev CA of the invention preferably constitures at least 80% of the carbonic anhydrase activity, more preferably at least 90%, even more preferably at least 95% and most preferably 100% of the carbonic anhydase activity. The composition comprising the metagenomics Logatchev CA of the invention can further comprise one or more excipients. An excipient in this context is to be understood as any auxilliary agent or compound used to formulate the composition and includes solvent (e.g., water), organic compounds, sugars, inorganic compounds, inorganic salts, fillers, pigments, waxes, carriers, stabilizers, surfactants, polymers, cross-linking agents, encapsulation agents, entrapment agents, immobilization agents, binders, magnetic compounds, adhesives, preservatives, buffers and the like.

The compositions may be prepared in accordance with methods known in the art and may be in the form of a liquid or a solid composition, or may be in the form of a semi-solid composition, such as a gel. The compositions may be in the form of a liquid or gel that forms a solid upon drying, such as a coating or paint or the like. The compositions may be stabilized in accordance with methods known in the art. For example, the enzyme composition may be formulated using methods known to the art of formulating technical enzymes and/or pharmaceutical products, e.g., into coated or uncoated granules or micro-granules or particles or other solid shapes that may have any suitable dimensions for production, delivery or use in the application, e.g., nano-particles, micro-particles or larger particles or materials. The polypeptide of the invention may thus be provided in the form of a granule, preferably a non-dusting granule, a liquid, in particular a stabilized liquid, a slurry or a protected polypeptide.

For certain applications, immobilization of the polypeptide may be preferred. An immobilized enzyme comprises two essential functions, namely the non-catalytic functions that are designed to aid separation (e.g., isolation of catalysts from the application environment, such as filtration or separation of the catalyst from a process liquid, reuse of the catalysts and control of the process) and the catalytic functions that are designed to convert the target compounds (or substrates), e.g., $CO_2$, to products, e.g., bicarbonate, within the time and space desired (Cao, Carrier-bound Immobilized Enzymes: Principles, Applications and Design, Wiley-VCH Verlag GmbH & Co. KGaA, Weinheim, Germany, 2005). An immobilized enzyme composition can be referred to as a biocatalyst. When an enzyme is immobilized it is made more easily separable from the reaction medium. An immobilized enzyme product can be separated from the application environment in order to facilitate its reuse, or to reduce the amount of enzyme needed, or to use the enzyme in a process where substrate is continuously delivered and product is continuously removed from proximity to the enzyme, which, e.g., reduces enzyme cost. Furthermore, enzymes are often stabilized by immobilization. Also, immobilization can change the physical properties of the enzyme in a way that makes it easier to deliver the enzyme in an optimal way to the reaction zone, or easier to control the amount and location of enzyme in the process, e.g., by changing the density of the biocatalyst to give a floating or sinking property, or to give the biocatalyst hydrophobic or hydrophilic properties, or to give the biocatalyst magnetic properties.

Processes for producing immobilized enzymes can be continuous or batch mode, depending on the requirements for process control. The method by which enzymes are immobilized can involve absorption onto or within a carrier (e.g., solids or gels), cross-linking of enzymes onto the surface or within a carrier, cross-linking of enzyme molecules without a carrier, covalent bonding to a carrier, and encapsulation or entrapment of enzyme molecules in a confined space by chemical or mechanical means. The immobilized enzyme can be produced to have a solid form, preferably with a moisture content or the presence of excipients that preserve the enzyme activity during storage and use. Alternatively, the immobilized enzyme can be produced as a in a semi-solid or physically heterogeneous form, as can be produced by chemically or mechanically restraining a portion of hydrated or dissolved enzyme in a confined space, such as by microencapsulation, e.g., in semi permeable membranes, or by inclusion in ultrafiltration systems comprising, e.g., hollow fiber modules, dialysis bags or envelopes, etc. Enzyme immobilization on porous carriers is also commonly used. This includes binding of the enzyme to the carrier, e.g., by adsorption, complex/ionic/covalent binding, or absorption of soluble enzyme on the carrier and subsequent removal of solvent. Cross-linking of the enzyme can also be used as a means of immobilization. Immobilization of enzyme by inclusion into a carrier is also industrially applied. (Buchholz et al., Biocatalysts and Enzyme Technology, Wiley-VCH Verlag GmbH & Co. KGaA, Weinheim, Germany, 2005). Specific methods of immobilizing enzymes such as carbonic anhydrase include, but are not limited to, spraying of the enzyme together with a liquid medium comprising a polyfunctional amine and a liquid medium comprising a cross-linking agent onto a particulate porous carrier as described in WO 2007/036235 (hereby incorporated by reference), linking of carbonic anhydrase with a cross-linking agent (e.g., glutaraldehyde) to an ovalbumin layer which in turn adhere to an adhesive layer on a polymeric support as described in WO 2005/114417 (hereby incorporated by reference), or coupling of carbonic anhydrase to a silica carrier as described in U.S. Pat. No. 5,776,741 or to a silane, or a CNBr activated carrier surface such as glass, co-polymerization of carbonic anhydrase with methacrylate on polymer beads as described in Bhattacharya et at, 2003, *Biotechnol. Appt Biochem.* 38: 111-117 (hereby incorporated by reference), or using globular protein and adhesive as described in US 2010/0068784. The carbonic anhydrase can also be immobilized using tags such as histidine-like tags (e.g., 6×His tag or HQ tag) or a cellulose binding module (CBM) (Liu et al, 2008, *Biotechnol. Prog.* 25: 68-74). The carbonic anhydrase can be fused with a silica condensing peptide and immobilized by autoencapsulation in a biosilica nanocomposite (Jo et al., 2014, Bioinspired silica nanocomposite with autoencapsulated carbonic anhydrase as a robust biocatalyst for $CO_2$ sequestration, *ACS Catal.* 4: 4332-4340).

Immobilized enzyme biocatalysts can take a broad range of physical forms, shapes and sizes, and may be adapted to meet the system performance requirements. Immobilized enzymes may be packaged or used in a variety of different forms, for example, immobilized enzyme particles can be enclosed in porous sheets, screens, baskets, papers, cloths or non-woven materials. The materials comprising immobilized enzymes can be fabricated into different shapes and structures, preferably shapes and structures that optimize the performance of the enzyme in the application, e.g., fabrication of immobilized enzyme particles together with materials in a paper, fabric, or non-woven filter form to entrap the enzyme particles and enhance gas-liquid contact. Enzymes can be immobilized by the process of electrospinning (Tran and Balkus Jr., 2012, Enzyme immobilization via electrospinning, *Topics in Catalysis,* 55(16): 1057-1069). Enzymes can be combined with the polymer or pre-polymer prior to electrospinning such that the enzymes become entrapped by the polymer molecule chains as a result of fiber solidification during the electrospinning process, enzymes can be immobilized onto electrospun fibers after the fibers are produced, enzymes can can be immobilized in electrospun fibers as one step of an immobilization process involving additional immobilization steps to produce a robust immobilized product, or enzymes can be confined inside hollow fibers produced by co-axial electrospinning (Cui et al., 2014, Biosequestration of $CO_2$ using carbonic anhydrase in situ encapsulated inside electrospun hollow fibers, *Chemical Journal of Chinese Universities-Chinese Edition* 35(9): 1999-2006). Fibers comprising enzymes produced by electrospinning can be used directly in processes of the present invention or can be combined with other materials to facilitate handling, use or performance, e.g., a hard surface, such as a packing material used in a gas-liquid contactor, or soft surface, such as a non-woven filter material, coated with enzyme-containing fibers produced by electrospinning. These immobilization processes and compositions can be combined with the carbonic anhydrase of the present invention.

An embodiment of the present invention is a composition comprising a matrix suitable for immobilization and a polypeptide having carbonic anhydrase activity selected from the group consisting of a) a polypeptide having an amino acid sequence corresponding to amino acid residues 1 to 226 of SEQ ID NO: 2 or amino acid residues 1 to 226 of SEQ ID NO: 5; or b) a polypeptide which is at least 60%, 65%, 70%, 75%, 80%, 85%, 90%, 91%, 92%, 93%, 94%, 95%, 96%, 97%, 98% or 99% identical to amino acid residues 1 to 226 of SEQ ID NO: 2 or amino acid residues 1 to 226 of SEQ ID NO: 5; or c) a fragment of (a) or (b) having carbonic anhydrase activity; or d) a polypeptide encoded by a nucleic acid sequence which hybridizes under low, medium, medium-high or high stringency conditions with:

i) a polynucleotide sequence encoding a mature polypeptide of SEQ ID NO: 2, or SEQ ID NO: 5; or ii) a polynucleotide sequence of SEQ ID NO: 1 or SEQ ID NO: 3; or iii) a subsequence of (i) or (ii), of at least 100 contiguous nucleotides, or iv) a complementary strand of (i) or (ii); or e) a polypeptide encoded by a nucleic acid sequence which, because of the degeneracy of the genetic code, does not hybridize with the polynucleotide sequence of SEQ ID NO: 1 or SEQ ID NO: 3, but which codes for a polypeptide having an amino acid sequence according to a) or b); or f) a polypeptide encoded by a nucleic acid sequence which is at least 60%, 65%, 70%, 75%, 80%, 85%, 90%, 91%, 92%, 93%, 94%, 95%, 96%, 97%, 98% or 99% identical to SEQ ID NO: 1 or SEQ ID NO: 3.

In embodiments of the present invention the carbonic anhydrase is immobilized in, on or together with a matrix, surface or material by chemical bonding, ionic bonding, physical bonding or entrapment or a combination of these. Non-limiting examples of a matrix, surface or material include those from the group: polymers, beads, fabrics, fibers, hollow fibers, membranes, particulates, porous surfaces, rods, structured packing, and tubes. Specific examples of suitable matrices, surfaces or substrates include alumina, bentonite, biopolymers, calcium carbonate, calcium phosphate gel, carbon, cellulose, ceramic supports, clay, collagen, glass, hydroxyapatite, ion-exchange resins, kaolin, nylon, phenolic polymers, polyaminostyrene, polyacrylamide, polyacrylonitrile (acrylic), polyethylene, polypropylene, polyester, polyurethane, polymer hydrogels, sephadex, sepharose, silica gel, silicone, precipitated silica, and TEFLON-brand PTFE. In embodiments, the matrices, surfaces or materials may be dried after combination with the enzyme. In an embodiment of the present invention carbonic anhydrase is immobilized on a nylon matrix according to the techniques described in Methods in Enzymology volume XLIV (section in the chapter: Immobilized Enzymes, pages 118-134, edited by Klaus Mosbach, Academic Press, New York, 1976), hereby incorporated by reference.

The polypeptide to be included in the composition may be stabilized in accordance with methods known in the art e.g., by stabilizing the polypeptide in the composition by adding an antioxidant or reducing agent to limit oxidation of the polypeptide or it may be stabilized by adding polymers such as PVP, PVA, PEG, sugars, oligomers, polysaccharides or other suitable polymers known to be beneficial to the stability of polypeptides in solid or liquid compositions or it may be stabilized by adding stabilizing ions, such as zinc (e.g., zinc chloride or zinc sulphate) which is present in the enzyme active site. A preservative, such as Proxel, or penicillin, can be added to extend shelf life or performance in application.

In a further embodiment the composition of the invention is a composition applicable in the capture of carbon dioxide.

Examples are given below of preferred uses of the compositions of the present invention. The dosage of the composition and other conditions under which the composition is used may be determined on the basis of methods known in the art.

Uses

Management and control of carbon dioxide ($CO_2$) concentration is important for a broad range of industrial, agricultural, medical and other technical processes. Conversion of $CO_2$ to alternative chemical forms, such as bicarbonate and carbonate, is one way to remove, separate, or extract $CO_2$ from a $CO_2$-containing medium, thereby controlling the $CO_2$ concentration in that medium. Conversion of $CO_2$ to an alternative chemical form can also function to retain the $CO_2$ in a $CO_2$-containing medium for a period of time, which can, for example, be useful for transporting $CO_2$ and for utilizing $CO_2$ in chemical and biochemical conversions that depend on the presence of $CO_2$, bicarbonate, or carbonate. Conversion of $CO_2$ to an alternative chemical form, such as bicarbonate, and reconversion from that alternative chemical form back to $CO_2$ is another way to control and manage the $CO_2$ concentration in processes, and provides a means to separate and transport $CO_2$ from one location to another location, and provides a means to separate $CO_2$ from a medium in one time period, and release the $CO_2$ from the medium in a later time period.

Carbon dioxide emissions are a major contributor to the phenomenon of global warming. $CO_2$ is a by-product of combustion and it creates operational, economic, and environmental problems. $CO_2$ emissions may be controlled by capturing $CO_2$ gas before emitted into the atmosphere. There are several chemical approaches to control the $CO_2$ emissions (A. Kohl and R. Nielsen, Gas Purification, $5^{th}$ ed., Gulf Professional Publishing, Houston, Tex., 1997). However, many of these approaches have drawbacks such as high energy consumption, slow processes, and use of ecologically questionable or toxic compounds.

Technical solutions for extracting $CO_2$ from gases, such as combustion gases, fuel gases, atmospheric gases or respiration gases, using carbonic anhydrases have been described in, for example, WO 2006/089423, U.S. Pat. No. 6,524,842, WO 2004/007058, WO 2004/028667, US 2004/0029257, U.S. Pat. No. 7,132,090, WO 2005/114417, U.S. Pat. No. 6,143,556, WO 2004/104160, US 2005/0214936, WO 2008/072979, WO 2008/095057, WO 2012/003336, WO 2012/025577, WO 2012/092984, WO 2012/154735, U.S. Pat. No. 7,998,714, WO 2013/151757, U.S. Pat. No. 8,871,008, WO 2015/126925, US 2015/0099289, and in the literature (e.g., Russo et al., 2013, Post-combustion carbon capture mediated by carbonic anhydrase, *Sep. Purif. Technol.* 107: 331-339; S. Salmon and A. House, "Enzyme-catalyzed solvents for CO2 separation," in *Novel Materials for Carbon Dioxide Mitigation Technology*, F. Shi and B. Morreale, Eds., Amsterdam, Elsevier B. V., 2015, pp. 23-86; and, S. Salmon and A. House, "Low-energy solvents for carbon dioxide capture enabled by a combination of enzymes and vacuum regeneration," Final Scientific/Technical Report for DE-FE0007741, U.S. Department of Energy, National Energy Technology Laboratory, 2015, DOI: 10.2172/1222645), which are herein incorporated by reference.

Generally, $CO_2$ scrubbing techniques operate by bringing a soluble or immobilized carbonic anhydrase into contact with $CO_2$ which either may be in a gas phase or a liquid phase. In the presence of water, carbonic anhydrase catalyses the conversion of $CO_2$ into bicarbonate ions which may be further protonated or deprotonated to carbonic acid and/or carbonate ions depending on the pH of the medium. The ions may either be utilized to facilitate growth of algae or microorganisms that utilize bicarbonate/carbonate as a carbon source, to induce a pH change in a surrounding medium or supply buffering capacity, to provide bicarbonate/carbonate as an active agent for subsequent chemical processes, or precipitated as a carbonate salt, or converted back into pure $CO_2$, which can then be used (for example in enhanced oil recovery, for production of urea, for food and beverage processing, or to supply $CO_2$ to greenhouses or cultivation ponds), released (for example from a contained life support environment such as a submarine, spacecraft, or artificial lung), compressed (for example for transportation through pipelines), or stored (such as in geological or deep oceanic formations or saline aquifers).

Furthermore, the use of carbonic anhydrase to catalyse the conversion of $CO_2$ to bicarbonate in the presence of cations, such as sodium and potassium, can help accelerate subsequent processes, such as conversion of bicarbonates to carbonates, resulting in more rapid conversion of $CO_2$ into useful alternative chemical forms. $CO_2$ conversion to bicarbonate can improve the productivity of biological systems that utilize the carbon from CO2 to produce chemical compounds (e.g., Atsumi et al., 2009, Direct photosynthetic recycling of carbon dioxide to isobutyraldehyde, *Nature Biotechnology* 27(12): 1177-1180). $CO_2$ conversion to carbonate, and the combination of carbonate with divalent cations such as calcium and magnesium, for example, is useful for sequestering, or storing, $CO_2$ in large quantities (e.g., Favre et al., 2009, Biocatalytic capture of $CO_2$ with carbonic anhydrase and its transformation to solid carbonate, *J. Molec. Cat. B; Enzymatic,* 60(3-4): 163-170). Production of carbonates is useful for the production of concrete, or for above-ground or below-ground $CO_2$ mineralization inside or as part of rocks or geologic formations, e.g., sub-surface limestone or basalt formations, also called "mineral sequestration," which help mitigate the negative impacts of $CO_2$ release to the atmosphere (e.g., US 2014/0234193). Preferably, sufficient cations and alkalinity to enable the carbonation reaction would be available at the mineralization site, however, these materials could also be delivered to the site, e.g., in the form of seawater, industrial brines, or aqueous waste streams comprising cations and alkalinity.

The presence of carbonic anhydrase in the systems and processes for $CO_2$ utilization can improve reaction efficiencies. For example, by rapidly converting $CO_2$, which has low water solubility, into bicarbonate, which has high water solubility, the presence of CA can help increase the carbon concentration in water systems used for growing algae, especially saline water systems comprising sodium or potassium cations, thereby improving algae growth and productivity. Delivery of CA into $CO_2$ sequestration sites, such as underground storage locations rich in divalent cations, can accelerate the mineralization process by accelerating the first step of the $CO_2$ to bicarbonate to carbonate reaction sequence, and ultimately resulting in precipitated carbonate-based solids. Similarly, in the presence of $CO_2$, CA can accelerate the removal or recovery of cations, especially divalent cations, from aqueous liquids, by accelerating the rate at which $CO_2$ is converted to its ionic forms and made available for ionic complexation with the cations to form solid bicarbonate or carbonate-based products that precipitate in the liquid or can be recovered by filtration or other solid-liquid separation techniques. Conversion of $CO_2$ into its ionic forms, such as bicarbonate, helps dissolve $CO_2$ into water-containing liquids and therefore increases the amount of $CO_2$ that can be loaded into and carried by these liquids. By accelerating the rate of $CO_2$ conversion to bicarbonate, CA can improve processes, such as the CarbFix process (Oelkers et al., 2008, Mineral carbonation of $CO_2$, *Elements* 4: 333-337), which requires large amounts of water to dissolve $CO_2$, by reducing the amount of water needed to transport a certain amount of $CO_2$ and by promoting the mineralization of $CO_2$.

The metagenomic Logatchev carbonic anhydrases described above are useful in a series of applications which are described in more detail below. When referring to metagenomic Logatchev carbonic anhydrase or carbonic anhydrase below it is intended to include all the carbonic anhydrases described in the present invention in particular if they fall within the claimed identities.

In particular metagenomic Logatchev carbonic anhydrase may be used for carbon dioxide extraction from $CO_2$ emission streams, e.g., from carbon-based or hydrocarbon-based combustion in electric generation power plants, or from flue gas stacks from such plants, industrial furnaces, stoves, ovens, or fireplaces or from airplane or car exhausts. Metagenomic Logatchev carbonic anhydrases may also be used to remove $CO_2$ in the preparation of industrial gases such as acetylene ($C_2H_2$), carbon monoxide (CO), chlorine ($Cl_2$), hydrogen ($H_2$), methane ($CH_4$), nitrous oxide ($N_2O$), propane ($C_3H_8$), sulfur dioxide ($SO_2$), argon (Ar), nitrogen ($N_2$), and oxygen ($O_2$). Metagenomic Logatchev carbonic anhydrase can also be used to remove $CO_2$ from a raw natural gas during the processing to natural gas. Removal of $CO_2$ from the raw natural gas will serve to enrich the methane ($CH_4$) content in the natural gas, thereby increasing the thermal units/m$^3$. Raw natural gas is generally obtained from oil wells, gas wells, and condensate wells. Natural gas contains between 1% to 10% $CO_2$ when obtained from geological natural gas reservoirs by conventional methods, but depending on the natural source or recovery method used may contain up to 50% $CO_2$ or even higher. Carbonic anhydrase can also be used to purify the natural gas such that it is substantially free of $CO_2$, e.g., such that the $CO_2$ content is below 1%, preferably below 0.5%, 0.2%, 0.1%, 0.05% and most preferably below 0.02%. In resemblance to the methane enrichment of natural gases, carbonic anhydrases can also be used to enrich the methane content in biogases. Biogases will always contain a considerable degree of $CO_2$, since the bacteria used in the fermentation process produce methane (60-70%) and $CO_2$ (30-40%). Biogas production may be performed using mesophilic or thermophilic microorganisms. Thermophilic strains allow the fermentation to occur at elevated temperatures, e.g., from 40° C. to 80° C., or from 50° C. to 70° C., or from 55° C. to 60° C. In such processes a heat-stable carbonic anhydrase is particularly useful to remove $CO_2$ from the methane. The present invention provides for the use of a metagenomic Logatchev carbonic anhydrase to reduce the carbon dioxide content in a biogas, preferably the $CO_2$ content is reduced such that it constitutes less than 25%, more preferably less than 20%, 15%, 10%, 5%, 2%, 1%, 0.5% and most preferably less than 0.1%. In a preferred embodiment the carbonic anhydrase is heat-stable. Furthermore, carbonic anhydrase may be applied in the production of syngas by removing the $CO_2$ generated by the gasification of a carbon containing fuel (e.g., methane or natural gas) thereby enriching the CO, $H_2$ content of the syngas. Where syngas production occurs at elevated temperatures the use of a heat-stable carbonic anhydrase is an advantage. The present invention provides for the use of a carbonic anhydrase to reduce the carbon dioxide content in a syngas production. Preferably, the $CO_2$ content is reduced such that it constitutes less than 25%, more preferably less than 20%, 15%, 10%, 5%, 2%, 1%, 0.5% and most preferably less than 0.1%. In a preferred embodiment the carbonic anhydrase is heat-stable. Preferably, the carbonic anhydrases to be used for $CO_2$ extraction as described above maintain residual activity of at least 30%, preferably above 40%, more preferably above 50%, more preferably above 60%, even more preferably above 70%, most preferably above 80%, most preferably above 85%, most preferably above 90%, most preferably above 95%, and even most preferably the residual activity is unchanged after incubation in 1 M $NaHCO_3$ buffer pH 8 at temperatures above 45° C., preferably above 50° C., above 55° C., above 60° C., above 65° C., more preferably above 70° C., most preferably above 80° C., most preferably above 90° C., most preferably above 100° C., most preferably above 105° C. and even most preferably above 110° C. for at least 15 minutes, preferably for at least 2 hours, more preferably for at least 24 hours, more preferably for at least 7 days, more preferably for at least 10 days, even more preferably for at least 14 days, most preferably for at least 30 days, even most preferably for at least 50 days at the elevated temperature. The temperature stability and/or longevity of the carbonic anhydrase can be increased to some extent by formulation, e.g., by immobilization and/or chemical or physical stabilization of the enzyme.

In a particular embodiment, the carbonic anhydrase of the invention, which may be used for $CO_2$ extraction as described above, maintains at least 85% activity when incubated for 15 minutes in 1M $NaHCO_3$ solution (approximately pH 8-10) in the temperature range 25-90° C. At 50° C., the enzyme maintains full activity over the pH range 4-11 for one day. After 10 days at 50° C., the enzyme maintains more than 50% activity over the pH range 4-11.

In an aspect of the present invention the $CO_2$ extraction from a $CO_2$-containing medium is performed in enzyme based bioreactors. Before the carbon dioxide-containing medium is processed in a bioreactor, it may be purified to free it from contaminants which may disturb the enzymatic reaction or interfere with bioreactor functionality in other ways, e.g., by clotting outlets or membranes. Gasses/multiphase mixtures emitted from combustion processes, e.g., flue gases or exhausts, are preferably cleared of ash, particles, $NO_x$ and/or $SO_2$, before the gas/multiphase mixture is passed into the bioreactor. Alternatively, $SO_2$ separation and $CO_2$ extraction can occur in the same reactor to improve system efficiency, because both separations are typically operated at alkaline process conditions. The raw natural gas from different regions may have different compositions and separation requirements. Preferably, oil, condensate, water and natural gas liquids, if present in the raw natural gas, are removed prior to the extraction of $CO_2$ in an enzyme based bioreactor. The $CO_2$ emitted from combustion processes or present in the raw natural gas may be extracted in the same process as the sulfur removal, or it may be extracted in a separate process. If the gas at this point exceeds the temperature tolerance of the carbonic anhydrase of the present invention, some degree of cooling may be needed. Preferably, the maximum temperature to which carbonic anhydrase is exposed during $CO_2$ extraction process whether it is the process temperature in the bioreactor or the feed gas temperature may be between 0° C. and 120° C. Preferably the maximum process temperature is between 40° C. and 120° C., more preferably between 45° C. and 110° C., more preferably between 50° C. and 100° C., more preferably between 55° C. and 90° C. even more preferably between 60° C. and 80° C., and most preferably between 65° C. and 75° C.

Reactors, systems and processes for gas separation, including $CO_2$ extraction, are well known in the art and are used commercially for various purposes (A. Kohl and R. Nielsen, Gas Purification, 5$^{th}$ ed., Gulf Professional Publishing, Houston, Tex., 1997). By selecting $CO_2$ absorption liquids (also called $CO_2$ absorption solvents) and operational conditions that are compatible with enzyme limitations, CAs of the present invention can be used in any solvent-based $CO_2$ extraction reactor to generate a bioreactor (a reactor comprising biological material such as an enzyme) for extracting $CO_2$ from gases, such as combustion gases, atmospheric gases, fuel gases, or respiration gases. CA can be present in these systems in an aqueous-soluble form, can be present as a suspended protein-based solid, and can be present in a form that is chemically or biochemically modified or combined with other materials. These different forms are collectively called biocatalysts.

Schematic diagrams for several common reactors (or gas-liquid contactors) used for $CO_2$ separation systems and processes are shown in FIGS. 1 to 6. These reactors can be used for $CO_2$ absorption from a gas into a liquid and for $CO_2$ desorption from a liquid to a gas. The reactors can be used for a single once-through unit operation or the gas or liquid streams or both can be recirculated from the outlet to the inlet of a reactor to provide for multiple passes of gas and liquid streams through a reactor. Multiple reactors can be arranged in $CO_2$ gas scrubbing systems in sequential or parallel arrangements, or both, to enable handling of large volumes of gas and liquid or provide high efficiency of $CO_2$ removal. Different types of reactors can be used to form gas scrubbing systems with many different configurations. For example, a counter-current packed reactor (illustrated by FIG. 1) can be used for $CO_2$ gas absorption into a liquid and can be arranged in a recirculating system together with the same type or another type of reactor, e.g., a membrane-based reactor (illustrated by FIG. 4), used for removing (desorbing) $CO_2$ from the liquid, and the process is repeated when the $CO_2$-lean liquid returns to the counter-current reactor. Many combinations and variations are possible. For continuous flow, the outlet liquid from one reactor travels to the inlet liquid of another reactor in the schematics shown in FIGS. 1 to 6. The reactors can be large or small.

Figure 7:
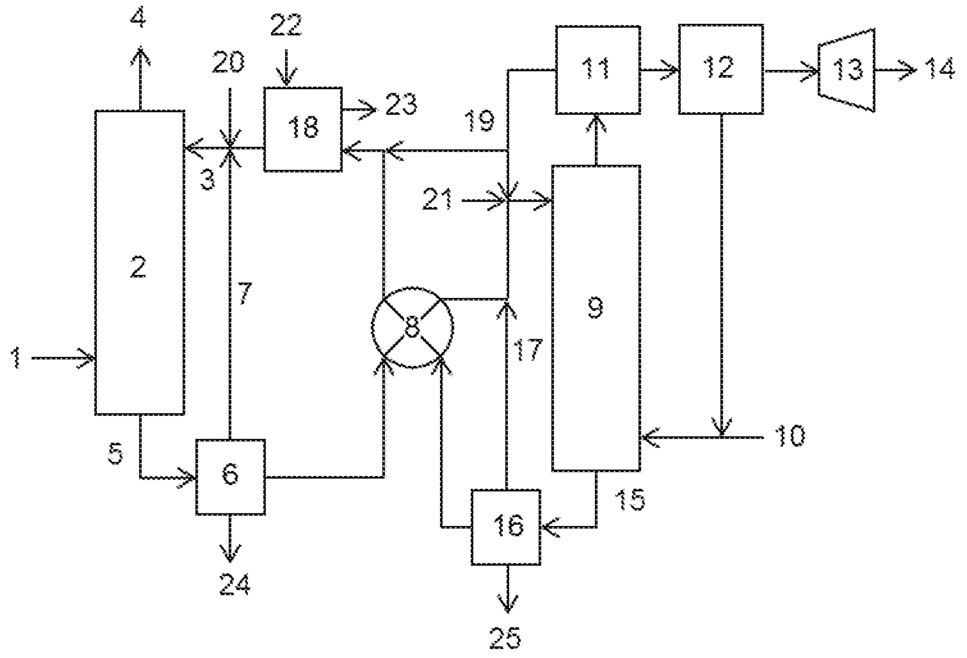
FIG. 7 shows a schematic diagram of an integrated $CO_2$ scrubbing system. In the system shown, $CO_2$-rich feed gas (1) enters near the bottom of the absorber (2) and flows upwards where it comes in contact with $CO_2$-lean absorption liquid (3) that enters the absorber near the top. Scrubbed gas (4), from which $CO_2$ has been removed, exits the absorber at the top. $CO_2$-rich absorption liquid (5) exits at the bottom of the absorber and (optionally) passes through a biocatalyst recovery unit (6) which separates the catalyst for recycling (7) and redelivery into the absorber along with the $CO_2$-lean absorption liquid (3). The main amount of $CO_2$-rich absorption liquid (5) exits the (optional) biocatalyst recovery unit (6) and travels to an optional temperature regulator (e.g., heat exchanger) (8) where the $CO_2$-rich absorption liquid is pre-heated before traveling to the desorber (9). The $CO_2$-rich absorption liquid enters near the top of the desorber and flows downwards. Heat is supplied to the desorber by any suitable means, e.g., a re-boiler, and optionally another desorption driving force such as a sweep gas (10) or vacuum (13), or a combination of these applied to the desorber causing extracted $CO_2$ to be released from the absorption liquid and exit the desorber, (optionally) passing through an absorption liquid condenser (11) to remove absorption liquid vapor from the gas stream, and (optionally) passing through a sweep gas condenser (12) to remove sweep gas compounds from the $CO_2$ gas stream prior to release, compression and/or use of the purified $CO_2$ gas (14). Sweep gas compounds separated in the sweep gas condenser (12) are optionally recycled and fed back to the desorber along with the provision of fresh sweep gas (10). $CO_2$— lean absorption liquid (15) exits the desorber, and (optionally) passes through a second biocatalyst recovery unit (16), which separates the biocatalyst for recycling (17) and redelivery into the desorber along with the $CO_2$-rich absorption liquid (5), before (optionally) passing through a temperature regulator (8), and (optionally) passing through a secondary $CO_2$ desorber (18) before returning to the absorber (3). Although the secondary $CO_2$ desorber may function by any of the known means of desorption, a preferred mode of operation for the secondary $CO_2$ desorber is as a secondary air sweep desorber utilizing a membrane-based design, in which $CO_2$-lean sweep gas (22), such as air is contacted with the $CO_2$-lean liquid (15) to further remove residual $CO_2$ remaining in the $CO_2$-lean liquid (15) and provide a very $CO_2$-lean liquid (3) for re-entry to the absorber. The secondary sweep gas (23) exiting the secondary $CO_2$ desorber (18) can be released to the atmosphere or can be used for a purpose, such as to supply air for combustion, e.g., when the $CO_2$ scrubber is installed at a power plant. Depleted biocatalyst and/or other depleted components of the absorption liquid can be added at various points in the process, such as at the locations indicated (20 and 21). Removal of samples for process monitoring and control of liquid levels as well as removal of insoluble contaminants can be carried out at various points in the process, such as at the locations indicated (24 and 25). Although not depicted in the diagram, it is understood that pumps to provide and control liquid flow, blowers to provide and control gas flow, and all relevant valves, meters, instrumentation and equipment for process control and monitoring can be installed and utilized at the needed locations. CA can be present in soluble or suspended particulate form in the liquid as it flows through the system and can be immobilized on the surfaces of structures, mixers or packing material immersed in or exposed to the liquid.

FIG. 7 shows an integrated $CO_2$ scrubbing system utilizing recirculation of the $CO_2$-absorption liquid between the absorber (2) and desorber (9) as well as optional units for biocatalyst separation (6 and 16) and recycling, optional utilization of sweep gas (10) in the desorption stage and optional utilization of secondary air sweep (18) prior to $CO_2$-lean liquid entry to the absorber. Because carbonic anhydrase improves the rate of $CO_2$ extraction, combining carbonic anhydrase with $CO_2$ extraction reactors enables reactor and process improvements such as smaller size and less expensive gas-liquid contactors (e.g., shorter absorption column), the use of process intensification approaches (e.g., horizontal spray reactors and rotating packed bed reactors), and use of low energy consuming and low volatility $CO_2$-absorption liquids, as well as overall lower operating temperatures compared to the conventional approaches.

One type of reactor uses liquid membranes. This may for example be reactors including hollow fiber membranes containing a liquid film as described in Majumdar et al., 1988, AIChE 34: 1135-1145; U.S. Pat. Nos. 4,750,918; 6,156,096; WO 04/104160. Such hollow fiber membrane-based designs are also sometimes termed hollow fiber liquid membranes (HFLM) and the $CO_2$ separation devices based on these have been termed hollow fiber contained liquid membrane (HFCLM) permeators. A common feature of HFCLM permeators is that the hollow fibers enclosing the feed and sweep gas streams are near (i.e., "tightly packed" or "immediately adjacent") to one another and they are enclosed in a single rigid treatment chamber to form one complete permeator. In such a design, a liquid surrounds the shell side of the tightly packed feed and sweep hollow fibers. Because the distance between the outside wall of one hollow fiber is very close to adjacent hollow fibers the thickness of the liquid layer between them is thin, like a membrane, and the composition of the liquid only allows certain components to pass, hence the term "liquid membrane" has been used to describe the liquid surrounding the hollow fibers. Contained liquid membrane permeators where the liquid film is sandwiched between two structural support membranes have also been described in the art (Cowan et al., 2003, *Ann. NY Acad. Sci.* 984: 453-469); this design essentially functions in the same way as the HFCLM. Contained liquid membrane permeators have also been used in combination with carbonic anhydrase as described in U.S. Pat. No. 6,143,556, WO 2004/104160, Cowan et al., 2003, *Ann. NY Acad. Sci.* 984: 453-469; and Trachtenberg et al., 2003, SAE international Conference on Environmental Systems Docket number 2003-01-2499. In these cases, the $CO_2$ desorption step takes place in the same enclosed treatment chamber as the absorption step. Another example describes an amine based $CO_2$ capture reactor based on absorber/desorber hollow fiber membrane modules (Kosaraju et al., 2005, *Ind. Eng. Chem. Res.* 44:1250-1258).

Another type of reactor uses direct gas-liquid contact. This may for example be conventional solvent based $CO_2$ capture reactors that are based on absorber/desorber column reactors (US 2008/0056972, Reddy et al., *Second National Conference on Carbon Sequestration, NETL/DOE*, Alexandria, Va., May 5-8, 2003). Example flow schemes for commercial direct gas-liquid contactor reactors that use alkanolamines (such as monoethanolamine, diethanolamine, and methyldiethanolamine) for $CO_2$ extraction are shown in A. Kohl and R. Nielsen, Gas Purification, 5$^{th}$ ed., Gulf Professional Publishing, Houston, Tex., 1997: 57-62. Example flow schemes for commercial direct gas-liquid contactor reactors that use alkaline salt solutions (such as potassium carbonate) for $CO_2$ extraction are shown in A.

Kohl and R. Nielsen, Gas Purification, $5^{th}$ ed., Gulf Professional Publishing, Houston, Tex., 1997: 334-340.

Direct gas-liquid contact reactors using carbonic anhydrase have been described in U.S. Pat. No. 6,524,843; WO 2004/007058, WO 2004/056455, U.S. Pat. No. 7,176,017, and US 2004/0059231. In these types of reactors the gas phase or multiphase mixture, is contacted with a liquid phase under conditions where the $CO_2$ in the gas phase is absorbed by the liquid phase where it is converted into bicarbonate by carbonic anhydrase. The bicarbonate enriched liquid is removed from the reactor by a continuous flow, to ensure that the equilibrium between $CO_2$ and bicarbonate is shifted towards continuous conversion of $CO_2$. The gas phase dissolution into the liquid phase is dependent on the surface contact area between the gas and liquid. A large contact area can for example be achieved by passing liquid and $CO_2$-containing gas through a high surface area packed column, tray or plate column or tower, by spraying small droplets of liquid through the $CO_2$-containing gas (i.e., a spray contactor), or by bubbling the $CO_2$-containing gas through the liquid (i.e., bubble tank or pond), or by combinations of these techniques. Packed columns can comprise packings such as raschig rings, berl saddles, lessing rings, intalox metal, intalox saddles, pall rings or engineered packings such as Q-PAC (Lantec Products, Inc., Agoura Hills, Calif. 91301). The packing materials may be comprised of a polymer such as nylon, polyester, polyethylene, polyetheretherketone, polypropylene, polystyrene or fluoropolymer (e.g., polytetrafluoroethylene), a ceramic such as silica, or a metal such as aluminium, carbon steel, or stainless steel, or a cellulose-based material such as wood or cotton fiber.

In reactor types where the liquid is continuously exchanged or when it is desirable to restrain carbonic anhydrase to one or more locations in the reactor, carbonic anhydrase may be retained in the reactor by various means. In packed columns the carbonic anhydrase can be immobilized on the packing material (for methods of immobilizing CA, see for example in WO 2005/114417, WO 2013/151757) or can be immobilized as particles (e.g., US 2015/0099289 and Yan et al., 2007, Fabrication of single carbonic anhydrase nanogel against denaturation and aggregation at high temperature, Biomacromolecules 8: 560-565) that recirculate from the outlet to the inlet of the packed column along with at least a portion of the liquid flow and avoiding travel through other parts of the system, or can circulate along with the $CO_2$-absorption liquid throughout the process, both absorption and desorption, due to enzyme stabilization imparted by the combination of enzyme with the immobilization matrix. The use of particles in gas-liquid contactors containing packing materials, baffles, and other internals is possible when the particles have the size and physical properties to flow along with the liquid. Small particles comprising CA are known to enhance $CO_2$ absorption, and is explained by the ability of carbonic anhydrase to rapidly catalyse the $CO_2$ hydration reaction together with the ability of small particles to be located and move around in the thin liquid film interface between the gas and liquid phases, allowing the substrate ($CO_2$) to rapidly come in contact with the CA catalyst (E. Alper and W. D. Deckwer, Some aspects of gas absorption mechanism in slurry reactors, in "Mass Transfer with Chemical Reaction in Multiphase Systems," E. Alper (ed.), Springer Science & Business Media, Dordrecht, 1983, pp. 199-224).

Different sized screens, filters or solid-liquid separation techniques, can be used to restrain CA enzyme, chemically or physically modified CA enzyme, or immobilized CA enzyme to particular operational units, regions, or locations in the $CO_2$ scrubbing system. Such techniques can also be used to restrain one type or mixture of CA biocatalysts in one reactor and another type or mixture of CA biocatalysts in another reactor zone. For example, this technique can be used to localize different CAs in the absorber and in the desorber. In "bubbling" reactors the carbonic anhydrase can be entrapped in a porous substrate, for example, an insoluble gel particle such as silica, silicone, urethane, alginate, alginate/chitosan, alginate/carboxymethylcellulose, or the carbonic anhydrase can be immobilized (by covalent bonds, ionic charges, entrapment or encapsulation) on a fixed solid packing, or can be immobilized on or in particles in suspension in the liquid, or the carbonic anhydrase can be chemically linked in an albumin or PEG network. Carbonic anhydrase can also be restrained to a particular location in the reactor by entrapment in a polymeric immobilization material which may comprise a micellar or inverted micellar material, such as described in WO 2010/037109, and may include chemical modification of the enzyme as part of the entrapment or immobilization technique (e.g., WO 2012/122404). CAs of the present invention can be immobilized by these and other techniques known in the art.

Spray contactors may include vertical or horizontal spray chambers, countercurrent spray columns, venturi scrubbers, ejectors or jet scrubbers, cyclone scrubbers, and spray dryers (A. Kohl and R. Nielsen, Gas Purification, $5^{th}$ ed., Gulf Professional Publishing, Houston, Tex., 1997: 418-427 and 604-616). Use of spray contactors is desirable for avoiding pressure drop and improving tolerance to solid particulates in the gas, such as may be important for atmospheric pressure post-combustion exhaust gas applications. However, to be most effective, the rate of $CO_2$ absorption in spray contactors must be fast, and carbonic anhydrase can provide the needed catalysis to achieve these fast rates.

$CO_2$ extraction in a direct gas-liquid contact reactor may involve a first absorption stage followed by optionally a subsequent desorption, precipitation, utilization, collection, regeneration or release stage. A general description of the absorption stage is as follows. When the absorption reactor is in operation, a water-containing liquid enters the reactor at one end, preferably the top, and flows to the other end, preferably the bottom, and the $CO_2$-containing gas stream (feed gas) enters the reactor at one end, preferably at the opposite end (the bottom) ("countercurrent") from the liquid and the gas passes through the liquid and exits, minus the $CO_2$ extracted into the liquid, through a gas outlet at the opposite end (preferably, the top of the reactor). The liquid that exits the absorption reactor is enriched in bicarbonate/carbonate ($CO_2$-rich liquid) and the exit gas is reduced in the $CO_2$ content compared to the feed gas. The $CO_2$-rich liquid may be processed in subsequent reactions, for example to generate pure $CO_2$ by passing through a desorption reactor, or produce carbonate precipitates such as CaCOs. The $CO_2$-rich liquid from the absorption reactor can also be utilized, e.g., to enhance algae growth, collected, e.g., by pumping the $CO_2$-rich liquid into a contained geological formation, released, e.g., by pumping the $CO_2$-rich liquid into the environment, such as release of bicarbonate liquid into seawater from a submarine life support system, evaporated or desalinated. The $CO_2$-rich liquid containing bicarbonate anion can be used in industrial processes, such as in the manufacturing processes for ammonium carbonate and ammonium bicarbonate, which are useful as fertilizer, or in processes for the removal and neutralization of acid gases such as sulfur dioxide.

The reactors described herein may involve an absorption stage, a desorption stage or a sequence of absorption and desorption stages in which carbonic anhydrase may catalyze either the hydration of $CO_2$ to bicarbonate or the dehydration of bicarbonate to $CO_2$ or both. The reactors can be combined with each other where each reactor constitutes a module. For example, a liquid membrane reactor can function as absorption module and the direct gas-liquid contact reactor can function as a desorption module or vice versa.

The terms "$CO_2$-lean" and "$CO_2$-rich" absorption liquid are terms used in the present invention to describe the relative amount of carbon (e.g., in the form of dissolved $CO_2$, chemically reacted $CO_2$, bicarbonate, carbonic acid and/or carbonate salt) present in the absorption liquid as it circulates through the process. As used herein, the term "$CO_2$-lean liquid" generally refers to absorption liquid entering an absorption unit. The term "$CO_2$-rich liquid" generally refers to a absorption liquid entering a desorption unit. It is understood that the term "$CO_2$-lean liquid" can also be applied to absorption liquid exiting a desorption module, and the term "$CO_2$-rich liquid" can also be applied to absorption liquid exiting an absorption unit. $CO_2$-rich liquid contains more carbon compared to $CO_2$-lean liquid within a given system at a given point in time. As used herein, the term "$CO_2$-rich gas" generally refers to a gas mixture with a relatively high $CO_2$ content, or it can be a pure stream of $CO_2$ gas. A $CO_2$-rich gas can be a feed gas. The term "$CO_2$-lean gas" generally refers to a gas mixture that is depleted in $CO_2$ content compared to the $CO_2$-rich gas from which at least a portion of $CO_2$ was removed. A $CO_2$-lean gas can be a gas that does not comprise $CO_2$, e.g., a pure stream of nitrogen gas. A $CO_2$-lean gas can be used as a sweep gas to help remove $CO_2$ from a $CO_2$-rich liquid.

Without limiting the scope of the present invention, FIG. 7 is provided to illustrate a general schematic of a $CO_2$ extraction system comprising both absorption and desorption units through which the $CO_2$ absorption liquid circulates as it removes $CO_2$ from a $CO_2$-containing gaseous phase (feed gas, 1) in the absorber (2), releases purified $CO_2$ gas (14) from the desorber (9), and recirculates back to the absorber. The term "feed gas" is often used in relation to $CO_2$ extraction reactors where it implies that $CO_2$ is removed from the $CO_2$ containing gaseous phase by contact with a $CO_2$-lean absorption liquid in the reactor. The feed gas may be at atmospheric pressure, or at pressures above or below atmospheric pressure. Selective solubility of $CO_2$ in the absorption liquid causes extraction of $CO_2$ from the feed gas into the absorption liquid in the absorber. In the desorber, $CO_2$ is released from the $CO_2$-rich absorption liquid by introducing a pressure difference (for example, a lower partial pressure of $CO_2$ in the desorber gas phase compared to that in the feed gas, such as can be achieved by applying vacuum in the desorber, or can be achieved by passing a sweep gas through the desorber, such as air or a condensable sweep gas) that lowers the solubility of $CO_2$ in the carrier liquid and/or applying heat, e.g., via a reboiler, steam or a sweep gas to drive $CO_2$ into the gas phase in the desorber. Heat for desorption can also be applied by inducing cavitation, e.g., through application of ultrasonic or other acoustic or vibrational energy, and by applying microwave or infrared energy to the $CO_2$-rich liquid. More than one desorption stage can be used to optimize the efficiency of $CO_2$ release. For example, heat can be applied in one stage of the desorber to remove and capture the bulk of the $CO_2$, followed by one or more secondary desorption stages, e.g., using air sweep, to remove additional $CO_2$ and 'polish' the liquid to a more $CO_2$-lean loading. Heat energy alone can be used to drive desorption such as is commonly used in monoethanol amine-based $CO_2$ extraction processes. For example the temperature in the desorber of a typical monoethanol amine-based $CO_2$ extraction is greater than 100° C. (e.g., 120° C.). Alternatively heat energy can be combined with pressure reduction to drive desorption. In this case the temperature in the desorber can be lowered. For example, together with a reduced pressure (e.g., vacuum) compared to the pressure in the absorber (e.g., atmospheric pressure), the desorber can be operated at 70° C. A difference in pH can be used to facilitate absorption and desorption, wherein $CO_2$ absorption into an aqueous medium is favored at more alkaline pH whereas $CO_2$ desorption from an aqueous medium is favored at a less alkaline (more acidic) pH. The range of relevant pH difference ("swing") between absorption and desorption depends on the particular process. For example, for the sake of illustration, $CO_2$ absorption into a bicarbonate-based carrier liquid can occur at pH 9 or above resulting in a decrease in the pH of that carrier liquid to below pH 9. Desorption of $CO_2$ from that carrier liquid can then occur at pH below pH 9.

A pressure difference between the absorber and the desorber can be established/occur when the pressure of the feed gas passing through the absorber is higher than the pressure of the gas phase in the desorber. In some cases, such as for natural gas upgrading, the gas pressure in the absorber is higher than in the desorber and the gas pressures in both the absorber and the desorber may be above atmospheric pressure. In other cases, the gas pressure in the absorber is above atmospheric pressure and the gas pressure in the desorber is at or below atmospheric pressure (i.e., equal to or less than 100 kPa). Alternatively, a pressure difference between the absorber and the desorber can be established/occur when the pressure of the feed gas (such as a coal-fired post-combustion flue gas) passing through the absorber is approximately at atmospheric pressure and the pressure of the gas phase in the desorber is below atmospheric pressure. In one embodiment of the present invention, the total gas pressure difference between the absorber and the desorber is at least about 35 kPa. Alternatively, a sweep gas comprising no or low concentration of $CO_2$, such as air, can be used to provide the driving force needed to release $CO_2$ from the $CO_2$-rich liquid as it passes through the desorber. $CO_2$ absorption and desorption can be operated in batch mode in a single reactor by first exposing the lean liquid in the reactor to $CO_2$-rich gas for a period of time, then applying desorption driving force options, such as heat, vacuum, acoustic or cavitation effects, or sweep gas, or combinations of these, to release $CO_2$ from the $CO_2$-rich liquid for a period of time to regenerate the $CO_2$-lean liquid. The sweep gas can be heated to provide both thermal and partial pressure driving forces for $CO_2$ release. The cycle can be repeated. Air sweep desorption can be desirable for applications where $CO_2$ separation is needed and the $CO_2$ being separated can be released to the atmosphere, for example when the released $CO_2$ is regarded as $CO_2$-neutral emissions, such as the $CO_2$ separated from methane during biogas upgrading.

One embodiment of the invention encompasses the use of condensable sweep gas compounds in the desorption stage of a $CO_2$ gas separation reactor. A typical solvent-based $CO_2$ gas separation reactor has two main stages: 1) an absorption stage, and 2) a desorption stage. In the absorption stage, $CO_2$ from the gas phase is absorbed by the liquid phase. In the desorption stage, $CO_2$ in the liquid phase is released to the gas phase. In order for $CO_2$ to be released from the liquid to the gas phase, a concentration gradient must exist, wherein the concentration (partial pressure) of $CO_2$ in the gas phase is less than the concentration (partial pressure) of $CO_2$ in the liquid phase. A "sweep" stream of non-$CO_2$ gas applied in the desorption stage can assist the mass transfer of $CO_2$ from the liquid to the sweep gas phase because the incoming sweep gas has no or low concentration of $CO_2$, causing $CO_2$ from the liquid phase to move in the direction of the low partial pressure of $CO_2$. One type of sweep gas is water vapour (water in the gas phase), such as is produced when aqueous liquids are boiled. However, considerable energy is required to boil water. Air or nitrogen gas can also be used as sweep gases, however there is no easy way to separate these gases from $CO_2$ after the desorption step, which may be necessary to obtain an isolated or purified $CO_2$ product. It is therefore desirable to utilize compounds that can perform as a sweep gas without the energy cost of boiling water and also have properties that allow these compounds to be easily separated from $CO_2$ after the desorption step to provide a purified stream of $CO_2$ gas and recovered sweep gas compounds that can be used for subsequent desorption operations.

The use of certain non-water-miscible volatile carriers together with $CO_2$ absorption solvents, such as aqueous MBA, in $CO_2$ stripping processes has been described (R. A. Frimpong, J. E. Remias, J. K. Neathery, M. Liu and K. Liu, Enhancing solvent regeneration with a high volatility liquid as a stripping carrier, Tenth Annual Conference on Carbon Capture & Sequestration, May 2-5, 2011, Pittsburgh, Pa.; Proceedings on CD-ROM, Exchange Monitor Publications & Forums, 4455 Connecticut Ave NW, Suite A700, Washington, D.C. 20008). These systems can include CA to enhance desorption efficiency by overcoming rate limitations that may exist in the conversion of bicarbonate to $CO_2$ during these processes, and CAs can be selected and engineered to be compatible with and withstand these processes whether or not they perform a specific catalytic role in these processes.

Condensable sweep gas compounds have the properties of a boiling temperature (equivalent to condensation temperature) that is substantially higher than the boiling temperature of $CO_2$, while at the same time, preferably, being lower than the boiling temperature of water. One such compound is dimethyl ether, which has a boiling point (b.p.) of −24° C. at 1 atmosphere pressure. This low boiling point facilitates the removal of dimethyl ether from reaction mixtures. Dimethyl ether is a gas at temperatures below the boiling point of water, and dimethyl ether will condense to a liquid at temperatures significantly higher than the sublimation temperature of $CO_2$ (−78.5° C., 1 atm). Therefore, a sweep gas containing a mixture of $CO_2$ and dimethyl ether can be passed through a chilled condenser at temperatures between −78° C. to −24° C. to cause the dimethyl ether to condense to a liquid and become trapped by the condenser while allowing the $CO_2$ to pass through the condenser as a purified gas stream. The dimethyl ether liquid can be recycled for reuse as a sweep gas. Dimethyl ether is a non-toxic, inexpensive compound, resistant to auto-oxidation compared to other alkyl ethers, and is considered as an alternative fuel or a renewable fuel (BioDME) from gasification of lignocellulosic biomass. Therefore, dimethyl ether is readily available for sweep gas applications. Dimethyl ether is combustible, therefore engineering controls are needed to prevent combustion during use. Such controls can be optimized to take advantage of the feature that the $CO_2$ compound being removed is itself non-combustible. Other examples of condensable sweep gas compounds are ethanol (b.p. 78.4° C.), methanol (b.p. 64.7° C.), acetone (b.p. 56° C.), propanol (b.p. 97-98° C.), isopropanol (b.p. 82.6° C.), tertiary butanol (b.p. 82.2° C.), and diethyl ether (b.p. 34.6° C.). In each case, appropriate engineering controls are needed to prevent unwanted combustion or decomposition, e.g., a risk associated with diethyl ether is decomposition to explosive peroxides. In a preferred embodiment, the condensable sweep gas compound is used in an amount that does not significantly diminish the $CO_2$-loading capacity achievable with the $CO_2$ absorption liquid.

In one preferred embodiment, dimethyl ether is the condensable sweep gas because the $CO_2$ desorption can be carried out at low temperatures, such as at ambient temperature, or in the range 0-90° C. or in the range 40-60° C., to enable a near-isothermal process between the absorber temperature (typically 40° C. for a post-flue gas desulfurization combustion flue gas, or a biogas) and the desorber temperature, which can be held at 40° C. or raised to a moderately higher temperature, for example to ensure solubility of the $CO_2$-rich liquid until desorption has occurred.

The condensable sweep gas can be contacted directly with the $CO_2$-containing liquid, or can be separated from the $CO_2$-containing liquid, such as by a $CO_2$-permeable membrane, analogous to an industrial process called “pervaporation,” where the liquid-phase feed is separated from the vapour-phase permeate by a membrane that is selective for the desired components. Vacuum is optionally applied on the permeate side to provide a low partial pressure of the desired component and drive the mass transfer of that component across the membrane.

In one embodiment, the condensable sweep gas compound directly contacts the liquid phase comprising the $CO_2$ to be removed. In a preferred embodiment, the presence of the condensable sweep has no or minimal impact on the amount of $CO_2$ that can be absorbed by the absorption solution (also called “loading capacity”).

In one embodiment, the condensable sweep gas compound is a volatile compound that is soluble in or miscible with water and has a lower boiling point than water, but does not form an azeotrope with water, e.g., methanol (b.p. 64.7° C.). The liquid phase comprising the $CO_2$ to be removed can comprise the water-soluble condensable sweep gas compound. In the reaction zone where desorption of $CO_2$ is carried out, the temperature is raised above the boiling point of the water-soluble condensable sweep gas compound, and the sweep gas compound evaporates from the water-based liquid, carrying $CO_2$ along in the vapour phase. Alternatively, the water-soluble condensable sweep gas compound can be raised to a temperature above its boiling point to convert it to a gaseous form, and the gaseous form can be contacted with the liquid phase comprising the $CO_2$ to be removed, preferably maintaining the temperature above the boiling point of the water-soluble condensable sweep gas.

In one embodiment, the condensable sweep gas compound is a volatile compound that may form an azeotropic mixture together with water and boils at a lower temperature than the boiling temperature of water, preferably in the presence of $CO_2$ absorption compounds. Upon exposure to heat, the volatile compound performs as a sweep gas as it vaporizes from the mixture. $CO_2$ dissolved in the liquid is carried along with the sweep gas at lower temperatures than if only water was present. This means less energy is required to remove $CO_2$ from the liquid. For example, water-miscible compositions, such as ethanol/water, when heated will volatilize towards a low-boiling azeotropic composition. In the case of ethanol/water, the azeotropic composition is 95.629 wt % ethanol, which can, for example, be prepared by mixing 95.629 g dry ethanol with pure water to make a total of 100 g solution (NIST Standard Reference Material 1828). At the azeotropic composition, the composition (of, e.g., ethanol and water) in the vapor phase is the same as the composition in liquid phase. Hence, boiling an azeotropic liquid at its azeotropic composition does not result in a change in the liquid composition. Ethanol boils at 78.4° C. and water boils at 100° C., whereas the azeotrope boils at 78.2° C., which is lower than either of its constituents. Upon heating (or distilling), compositions of ethanol and water, wherein the proportion of ethanol is less than the azeotropic composition, will release relatively more ethanol into the gas phase than water, and the composition of the boiling liquid phase will become less concentrated in ethanol and more concentrated in water. Meanwhile, the proportion of ethanol in the gas phase will increase, and the collected condensate will have a higher proportion of ethanol compared to the initial boiling liquid composition. Therefore, ethanol can perform the function of a sweep gas by vaporizing at a lower temperature compared to water.

In one embodiment, the condensable sweep gas has low solubility in water or is easily separated from water to avoid the sweep gas component being retained by the $CO_2$-lean liquid as it exits the desorption stage. For example, tertiary butanol is not miscible with water and has a boiling point of 82° C., which is lower than the boiling point of water. Therefore, tertiary butanol can function as a sweep gas and can be subsequently easily separated from water, e.g., in a condensation tank that provides for liquid-liquid separation. Additives, such as surfactants, can be present to enhance the miscibility of the sweep gas compound with water during the $CO_2$ extraction stage to enhance the effectiveness of the sweep gas in removing $CO_2$. Also, additives, such as surfactants, can be present to enhance the interaction of $CO_2$ with the sweep gas, or reduce the interaction of $CO_2$ with the $CO_2$ absorption solution, in either case leading to enhanced release of $CO_2$ from the $CO_2$ absorption solution.

The ability to conduct low temperature desorption with a condensable sweep gas is especially beneficial when combined with a catalyst, such as carbonic anhydrase, to minimize rate limitations in the conversion of bicarbonate to $CO_2$ when $CO_2$ desorption is carried out at low temperature.

In one embodiment, the presence of carbonic anhydrase in the liquid or in contact with the liquid means that a constant supply of dissolved $CO_2$ will be available in the solution as the result of the CA catalyzed conversion of bicarbonate to $CO_2$ in aqueous solutions comprising bicarbonate. The resulting vapour phase contains $CO_2$, $H_2O$ and sweep gas compound (e.g., ethanol). Water and ethanol are recovered from the vapour phase in a cold trap, resulting in a pure $CO_2$ gas at the exit.

The absorber and desorber shown schematically in FIG. 7 can be at essentially the same ("isothermal") temperature or at different temperatures. Metagenomic Logatchev carbonic anhydrase may be present in only the absorber or the desorber or both. Regeneration of $CO_2$ using vacuum (low pressure) at low temperatures, e.g., 70° C. in the desorber where a high temperature carbonic anhydrase such as metagenomic Logatchev carbonic anhydrase is present is a further embodiment of the present invention. Carbonic anhydrase in such a process catalyses both absorption and desorption of $CO_2$ to and from the absorption solvent. When the absorber and desorber are at different temperatures, a temperature regulator (e.g., heat exchanger) can be used to conserve energy in the process.

In a further illustration, a modification of the vacuum carbonate process for $H_2S$ absorption (A. Kohl and R. Nielsen, Gas Purification, 5th ed., Gulf Professional Publishing, Houston, Tex., 1997: 383-388) has been described for $CO_2$ extraction (US 2007/0256559) and disclosed in combination with carbonic anhydrase (Lu et al., DOE Project No. DE-FC26-08NT0005498, NETL CO2 Capture Technology for Existing Plants R&D Meeting, Mar. 24-26, 2009, Pittsburgh, Pa.). In this illustration, atmospheric pressure power plant flue gas contacts aqueous potassium carbonate and carbonic anhydrase in the absorber column at temperatures in the range 40 to 60° C., where carbonic anhydrase improves the rate of $CO_2$ hydration to bicarbonate in the carrier liquid. The $CO_2$-rich absorption liquid is pumped to a desorber column (or "stripper") where $CO_2$ is released from the absorption liquid by a combination of low pressure (e.g., 14-55 KPa) and the application of heat (e.g., 50-70° C.) obtained by directly injecting low pressure, low quality exhaust steam from a low pressure steam turbine of the power plant. Carbonic anhydrase from metagenomic Logatchev of the present invention is especially suitable for use in the described modified vacuum carbonate process because metagenomic Logatchev CA can tolerate temperatures both in the absorber and the desorber, meaning that, metagenomic Logatchev CA can recirculate along with the absorption liquid through both absorption and desorption stages of the process.

A further type of reactor uses membranes in combination with $CO_2$ hydration catalysis by CA followed by precipitation. In one case, $CO_2$ is removed from a gaseous stream by passing the gaseous stream through a gas diffusion membrane into solution where conversion to bicarbonate and, subsequently, to carbonate is accelerated by passing the $CO_2$ solution over a matrix that contains CA and adding a mineral ion to cause precipitation of the carbonic acid salt (U.S. Pat. No. 7,132,090). It has been shown that CA can not only catalyse the $CO_2$ hydration/dehydration reaction but can also promote the precipitation of calcium carbonate (Mirjafari et al., 2007, *Ind. Eng. Che. Res.,* 46: 921-926).

A further type of reactor removes $CO_2$ from ambient air. A reactor designed to remove $CO_2$ from ambient air have been reported (Stolaroff et al. 2008 *Environ. Sci. Technol,* 42: 2728-2735), however this reactor does not utilize carbonic anhydrase. Without being bound by the design of the reported ambient air reactor, a CA combined with suitable absorption liquids as disclosed in the present invention, could be used in such a reactor or in other reactor designs as described herein. A heat stable carbonic anhydrase is especially useful because exposure of the reactor to environmental conditions, such as sunlight, may increase the liquid temperature requiring the CA to have good thermostability, therebyavoiding the need to cool the reactor. This illustrates a situation where the process of extracting $CO_2$ from the $CO_2$-containing medium requires CA to function at or tolerate higher temperatures than the initial temperature of the $CO_2$-containing medium, such as ambient air, which may be cold at night (below 10° C.) and hot during the day (above 45° C.).

The different membrane reactors and direct gas-liquid contact reactors described herein as well as other alternatives may be applied in a carbon dioxide extraction process, where the absorption process and desorption process occur in at least two steps. Such reactors generally comprise the following elements: a) at least one absorption unit, which may comprise a gas inlet zone and/or a gas outlet zone; b) at least one desorption unit comprising a gas outlet zone; c) a $CO_2$ absorption liquid; and d) means for connecting the absorption unit(s) and the desorption unit(s) such that the absorption liquid can pass from the absorption unit(s) to the desorption unit(s). Optionally the means for connecting the absorption and desorption units is a circuit, allowing the absorption liquid to be returned to the absorption unit once it has passed through the desorption unit. One or both of the units may comprise at least one $CO_2$-permeable membrane which separates a gas phase from a liquid phase, such as described in WO 2010/014773 and WO 2010/014774. This type of membrane unit is also termed a gas-liquid membrane (GLM) unit. The GLM unit may, e.g., be in the form of a hollow fiber membrane, a flat sheet membrane or a spiral-wound membrane. The GLM unit may either function as an absorber unit and/or a desorber unit. Alternatively, one of the units may be a GLM unit and the other unit may be composed such that the gas and liquid phases are in direct contact or in other words the gas-liquid interface is not separated by a membrane. This type of unit is also termed a direct gas-liquid contact (DGLC) unit or just a direct contact (DC) unit. The DGLC unit may, e.g., be in the form of a column filled with packing material that allows for gas-liquid contact, and/or a liquid-containing vessel equipped with an inlet for exposing gas to the liquid (such as a bubble column), and/or a liquid-spray (such as a spray tower) and/or an aerator unit and/or a falling film. The DGLC unit may either function as an absorber unit or a desorber unit. Bubble cap system, sieve plate system, disk-and-doughnut column and packed column are examples of the internals found in DGLC units.

The reactor types described above may be operated at any desired temperature. In one embodiment, the reactor is operated with a temperature of the liquid in contact with and/or comprising carbonic anhydrase between 0° C. and 120° C. or 5° C. and 110° C., more preferably between 10° C. and 100° C., more preferably between 20° C. and 95° C., more preferably between 30° C. and 90° C., more preferably between 40° C. and 85° C., more preferably between 40° C. and 80° C., more preferably between 40° C. and 75° C., and more preferably between 40° C. and 70° C., and most preferably between 40° C. and 60° C.

The absorption and desorption rates of $CO_2$ are dependent on the pH in the absorption liquid. In the reactor types described in relation to the present invention the pH of the $CO_2$-lean absorption liquid is between pH 4 to 12, preferably above pH 7 (as measured at room temperature, e.g., 20-25° C.), more preferably above pH 8, more preferably between 8 and 12, more preferably between 8 and 10.5, more preferably between 8.5 and 10, even more preferably between 9 and 9.5. The hydration of $CO_2$ to to bicarbonate during absorption results in release of a proton causing the pH of the absorption liquid to decrease as the carbon content of the $CO_2$-rich absorption liquid increases. The extent of pH decrease depends on the buffering capacity of the absorption liquid and the amount of $CO_2$ absorbed. In a preferred embodiment of the present invention the absorption liquid is a bicarbonate-based buffer or a carbonate-based buffer, such as lithium bicarbonate, sodium bicarbonate, potassium bicarbonate, cesium bicarbonate, ammonium bicarbonate or another suitable salt of the bicarbonate, or lithium carbonate, sodium carbonate, potassium carbonate, cesium carbonate, ammonium carbonate or another suitable salt of the carbonate, or combinations of bicarbonate and carbonate compounds, where, depending on the pH, greater or lesser amount of carbonate and/or carbonic acid will exist together with bicarbonate.

In one embodiment of the present invention, the $CO_2$-rich absorption liquid passes through a desorption stage where the pH of the $CO_2$-rich absorption liquid will increase as the $CO_2$ is released. In order to recirculate absorption liquid through such an absorption-desorption system, it is preferred that the pH of the absorption liquid returns to the pH of the $CO_2$-lean absorption liquid before again passing through the absorption stage.

In a preferred embodiment of the present invention the reactor is equipped with means for regulating pH in the absorption liquid. This can be performed in several ways. One way is to add an alkaline substance to the absorption liquid, e.g., at one of the auxiliary components addition points (20) indicated in FIG. 7, using automatic pH adjustment equipment such as an automatic titrator. The alkaline substance preferably has a similar composition (e.g., concentration of solvent, ionic strength, amount of carbonic anhydrase, etc.) as the absorption liquid circulating in the system and can be added at any time before absorption for adjustment of pH. Similarly a neutral to acidic substance can be added to the absorption liquid any time before desorption, e.g., at one of the auxiliary components addition points (21) indicated in FIG. 7. Extra absorption liquid can be removed from the system if needed, e.g., at one of the removal points (24 and 25) indicated in FIG. 7.

In the $CO_2$ capture processes described herein the metagenomic Logatchev CAs of the present invention may be combined with one or more other CAs. Different process steps in the overall $CO_2$ scrubbing process may require optimization of operating conditions, e.g., temperature, pH, carrier liquid compositions, pressure and so forth. The CAs of the present invention may be combined with other CAs operating at different optimal conditions and which are suitable for use in the $CO_2$ scrubbing process. For example, one CA can circulate throughout the system along with the absorption liquid and a different CA can be immobilized at one or more locations in the system.

The CAs of the present invention and bicatalyst based bioreactors described herein comprising a CA of the present invention also find more unconventional applications, such as in pilot cockpits, submarine vessels, aquatic gear, safety and firefighting gear, astronaut space suits and artificial lung devices to keep breathing air free of toxic $CO_2$ levels. Other applications are to remove $CO_2$ from confined spaces, such as to reduce hazardous $CO_2$ levels from inside breweries and enclosed buildings carrying out fermentation, and from $CO_2$ sensitive environments like museums and libraries, to prevent excessive $CO_2$ from causing acid damage to books and artwork. Another application is to remove $CO_2$ from hot ambient air, e.g., in a desert. In this case the carbonic anhydrase could for example be comprised in a reactor suitable for extracting $CO_2$ from ambient air as described in Stolaroff et al. 2008 *Environ. Sci. Technol,* 42, 2728-2735, such a reactor can, for example, take the form of an "artificial tree" or a windmill as described in WO 2008/041920.

Metagenomic Logatchev CA can be used alone as a $CO_2$ extraction biocatalyst together with a water-based absorption liquid or it may optionally be combined with conventional $CO_2$ extraction technologies such as chemical absorption via amine-based solvents or aqueous ammonia or physical solvents such as Selexol™ (Union Carbide) or polyethylene glycol ethers. In a further embodiment of the present invention, metagenomic Logatchev CA is combined with one or more $CO_2$ absorbing compounds, such as amine-based compounds, for example, aqueous alkanolamines including monoethanolamine (MBA), diethanolamine (DBA), N-methyldiethanolamine (MDEA), 2-amino-2-hydroxymethyl-1,3-propanediol (Tris or AHPD), diglycolamine (DGA), 2-amino-2-methyl-1-propanol (AMP), Methylmonoethanolamine (MMEA), Dimethylmonoethanolamine (DMMEA), diethylmonoethanolamine (DEMEA), diisopropanol amine (DIPA), triisopropanolamine (TIPA), aqueous soluble salts (e.g., sodium or potassium salts) of N-methylaminopropionic acid or N,N- dimethylaminoacetic acid or N-methylalanine, N-methylglycine, N,N-dimethylglycine, beta-alanine (3-aminopropanoic acid) or other natural or modified amino acids (e.g., N-substituted amino acid derivatives), 2-(2-aminoethylamino)ethanol (AEE), triethanolamine (TEA) or other primary, secondary, tertiary or hindered amine-based solvents including those described on pages 7 to 9 of U.S. Pat. No. 4,112,052 (hereby incorporated by reference), or aqueous soluble salts of glycine (e.g., sodium or potassium glycinate) and taurine or other liquid $CO_2$ absorption compositions such as aqueous solutions comprising NaOH, KOH, LiOH, alkali-metal carbonate salts (e.g., lithium, sodium, potassium, or ammonium), alkali-metal bicarbonate salts, alkali-metal phosphate salts, or borate salts, such as sodium tetraborate decahydrate (borax), at different ionic strengths, molar concentrations (ranging from dilute solutions to highly concentrated solutions, up to the solubility limit of the salts, which may vary based on the temperature) or aqueous electrolyte solutions and promoters such as piperazine, or polyethylene glycol ethers, or a blend of them or analogs or blends thereof. The aqueous soluble salts and solvents may be used in combinations with each other and may be combined with pH buffering and mineral sequestering compounds, such as phosphate salts, polyphosphate salts and borate salts, to provide mixed salt solutions, such as potassium or sodium bicarbonate with potassium or sodium phosphate. The aqueous soluble salts and solvents may be combined with simple electrolytes (e.g., alkali halides, such as NaCl, KCl, and metal halides, such as ZnCl) and sulfate salts, such as sodium sulfate and potassium sulfate. Preferably the $CO_2$ absorption composition comprises sufficient concentration of aqueous-soluble salts, e.g., NaCl, to stabilize and optimize the catalytic activity of metagenomic Logatchev CA. The combination of metagenomic Logatchev CA with $CO_2$ absorption components may be applied in the bioreactors described herein andmay be applied to already existing $CO_2$ scrubbing facilities based on conventional techniques. In conventional bioreactors, the concentration of alkanolamines is typically 15-30 weight percent. In an embodiment of the present invention the concentration of alkanolamines can be in the conventional range or preferably at a lower concentration, such as preferably below 15% (V/V), more preferably below 12%, 10%, 8%, 6%, 5%, 4%, 3%, 2%, 1%, 0.5%, 0.2% and most preferably below 0.1% (V/V).

Certain simple amino acids and amines are known to activate α-CAs (Akdemir et al., 2013, The extremo-α-carbonic anhydrase (CA) from *Sulfurihydrogenibium azorense*, the fastest CA known, is highly activated by amino acids and amines, *Bioorg. Med. Chem. Lett.* 23: 1087-1090), and are herein incorporated by reference. They include D-Phe, L-DOPA, L- and D-Trp, dopamine, serotonin, L- and D-His, L-Phe, L-Tyr, 2-pyridyl-methylamine, L-adrenaline, D-DOPA, D-Tyr, and deveral heterocyclic amines.

In conventional processes, corrosion and oxidation inhibitors, such as contained in Fluor Daniel's proprietary Econ-Amine FG solvent, are added to provide for increasing the amine concentration while reducing the risk of corrosion. Inorganic corrosion inhibitors include vanadium (e.g., sodium metavanadate), antimony, copper, cobalt, tin, and sufur compounds. Organic corrosion inhibitors include thiourea and salicylic acid.

Other auxiliary absorption liquid components can include wetting agents, chelating agents (e.g., ethylenediamine tetraacetic acid, polyphosphate salts), antifoams, viscosity reducers, and other compounds capable of increasing the flux of $CO_2$ into or out of the carrier liquid.

In conventional processes, techniques to reduce and/or avoid foam formation are commonly employed. These include removal of foam-causing impurities prior to $CO_2$ extraction and use of antifoaming agents and foam inhibitors such as silicone compounds or high-boiling alcohols such as oleyl alcohol or octylphenoxyethanol (A. Kohl and R. Nielsen, Gas Purification, $5^{th}$ ed., Gulf Professional Publishing, Houston, Tex., 1997: 224-230).

Another aspect of the present invention relates to biogas production where the $CO_2$ extraction is performed directly in the biogas fermentation broth, as an alternative to passing the biogas through a bioreactor as described above. By adding metagenomic Logatchev CA to the anaerobic broth, as an additive in a biogas fermentation medium, more $CO_2$ from the gas phase can be converted into bicarbonate, which is the substrate for methane production by the methanogenic Archaea. Particularly, the genus *Methanosarcina* is frequently present in thermophilic biogas digesters (Mladenovska and Ahring, 2000, *FEMS Microbiol. Ecol.* 3: 225-229). It has been shown for *Methanosarcina thermophila*™-1 that bicarbonate may be a limiting factor for the methane production, for example cultures of *M. thermophila*™-1 grown in low bicarbonate solution (0.6 mM) showed a considerable lag phase (i.e., methane production began later) when compared with cultures containing ten times higher bicarbonate dosages (6 mM). Additionally, the total yield of methane was 25 times less at the lower bicarbonate dosage (Murray and Zinder, 1985, *Appl. Environ. Microbiol.* 50: 49-55). Consequently, a heat-stable carbonic anhydrase is particularly useful when the biogas production is performed at elevated temperatures using one or more thermophilic microorganisms, for example methanogens like *Methanosarcina* sp. that can use $CO_2$/biocarbonate as carbon source for growth and methanogenesis.

A further embodiment of the present invention is use of a metagenomic Logatchev CA to enhance growth of algae and other aquatic plants that utilize bicarbonate as a carbon source by catalyzing the conversion of $CO_2$ to bicarbonate in or for delivery to the aquatic plant environment. This approach can, for example, be used to simultaneously remove $CO_2$ from a combustion exhaust gas, such as a flue gas, and provide $CO_2$ for conversion to bicarbonate by contacting the exhaust gas with liquid from a cultivation pond. Certain approaches to cultivating algae and aquatic plants involve use of enclosed tubes or shallow troughs or ponds in which heat from sunlight raises the water temperature. Hence a heat stable carbonic anhydrase is particularly useful at the elevated cultivation temperatures.

The present invention is further described by the following examples that should not be construed as limiting the scope of the invention.

EXAMPLES

Chemicals used as buffers and substrates were commercial products of at least reagent grade.

Example 1

Cloning and Expression of Logatchev Carbonic Anhydrase in *B. subtilis*

The gene of a carbonic anhydrase (referred to as Logatchev CA; DNA shown as SEQ ID NO: 1, and protein shown as SEQ ID NO: 2) was identified as a metagenomic sequence obtained from the Logatchev hydrothermal vent (Perner et al., 2013, *Environ. Microbiol.* 15: 1551-1560). Based on the sequence, the Logatchev CA is an α-type carbonic anhydrase.

A synthetic polynucleotide encoding the Logatchev CA (nucleotides 82 to 759 of SEQ ID NO: 3) was designed and the codon usage was optimized for *B. subtilis*. The codon optimization process was performed as described in WO 2012/025577.

The alkaline protease signal peptide from *B. clausii* (encoded by nucleotides 1 to 81 of SEQ ID NO: 3) was cloned in frame to the optimized Logatchev CA nucleotide sequence.

The synthetic Logatchev CA gene was cloned into a suitable expression vector resulting in plasmid pLogatchev.

Figure 8:
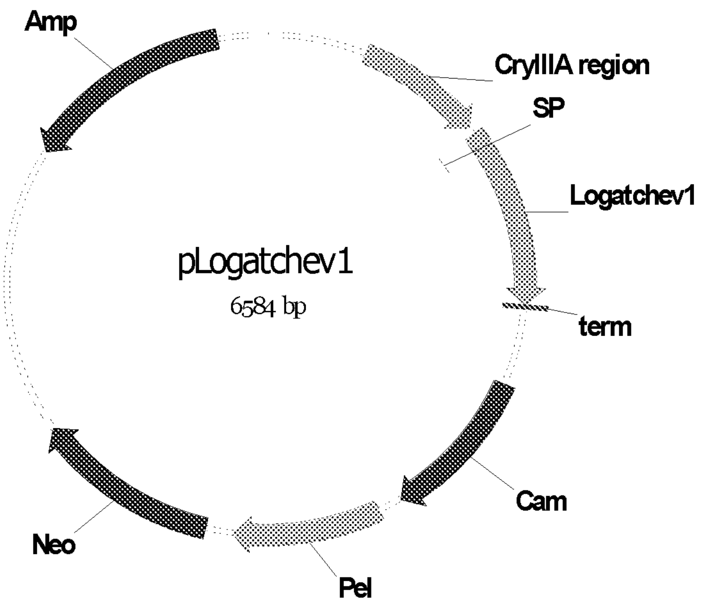
FIG. 8 shows pLogatchev plasmid map.

In the expression vector, the CA gene was expressed by control of a triple promoter system as described in WO 2012/025577. *E. coli* TOP10 cells were transformed with plasmid pLogatchev and one correct clone was selected using methods known in the art. Competent *B. subtilis* cells were transformed with the plasmid isolated from the selected *E. coli* clone, the CA gene construct in the plasmid integrated into the *B. subtilis* chromosome by homologous recombination into the pectate lyase gene locus (denoted Pel in FIG. 8).

Chloramphenicol resistant *B. subtilis* clones were analyzed by DNA sequencing to verify the correct DNA sequence of the construct. The translated protein sequence is shown as SEQ ID NO: 4, where amino acid −27 to −1 corresponds to the alkaline protease signal peptide from *B. clausii*, and amino acids 1 to 226 corresponds to the predicted mature Logatchev CA (SEQ ID NO: 5).

One expression clone was selected and was cultivated on a rotary shaking table in deep well plates each containing 2 ml yeast extract rich media supplemented with 6 mg/l chloramphenicol. The clone was cultivated for 3 days at 26° C. It was determined that there was very high CA activity in the culture broth solution using a CA activity assay essentially as described in Example 3.

To semi-purify the heat-stable Logatchev CA from endogenous *B. subtilis* enzymes in the culture broth, the cell free broth was incubated at 80° C. for 15 min and the solution was centrifuged for 10 min at 10.000×g. The soluble, thermostable Logatchev CA remained in the supernatant, whereas the heat treatment caused co-expressed non-thermostable proteins to precipitate, and the precipitated solids were separated as a pellet during centrifugation. The recombinant CA protein expression and successful purification was monitored by SDS-PAGE analysis.

Example 2

Cloning and Expression of Site-Directed Mutants of Logatchev CA in *B. subtilis*

The pLogatchev plasmid expressing the Logatchev CA backbone was constructed as described in Example 1. Based on the expression construct from Example 1 we introduced site-directed mutations in the gene to even further optimize the thermostability of the CA enzyme. Mutations were introduced into the Logatchev CA amino acid sequence by In-Fusion multiple fragment cloning in *E. coli* TOP10 according to Table 1, to generate Variant1, Variant2, Variant3 and Variant4. All constructs were constructed with the alkaline protease signal peptide, transformed into *B. subtilis* and recombinantly expressed as described in Example 1.

Expression levels of the Logatchev CA and variants thereof were analyzed by SDS-PAGE. Visual inspection of the gel showed that the mutations had little effect on the CA enzyme yield, though variant SEQ ID NO: 9 expressed with lower CA enzyme protein yield compared to SEQ ID NO: 5.

TABLE 1

Logatchev CA variants; mutations made in the Logatchev CA amino acid sequence.

| Carbonic anhydrase | Amino acid sequence | Mutations |
|---|---|---|
| Logatchev CA | SEQ ID NO: 5 | wildtype (no mutations) |
| Variant1 | SEQ ID NO: 6 | I99V |
| Variant2 | SEQ ID NO: 7 | R40S + I99V |
| Variant3 | SEQ ID NO: 8 | R40S + G56L + I99V |
| Variant4 | SEQ ID NO: 9 | D19F + K21R + R40S + G56L + I99V |

Example 3

Detection of Carbonic Anhydrase Activity

A test for the detection of CA activity was described by Wilbur and Anderson (Wilbur and Anderson, 1948, Electrometric and colorimetric determination of carbonic anhydrase, *J. Biol. Chem.* 176: 147-154) and was conducted as further described in WO 2012/025577. Briefly, this test monitors the rate of reaction between $CO_2$ and water by detecting the concurrent release of protons. The rate of release of protons is measured, for example, by the time required for the pH of the solution to change to a defined endpoint pH, or by measuring the time required for a pH indicator in the solution to change to a defined endpoint color. In the presence of CA as a catalyst, less time will be required to reach the endpoint compared to the uncatalyzed reaction. One unit is defined after Wilbur [1 U=(1/tc)−(1/tu)×1000] where U is units and to and tu represent the time in seconds for the catalyzed and uncatalyzed reaction, respectively. These units are also termed Wilbur-Anderson units (WAU).

Samples of cell-free broths from *B. subtilis* cells expressing the wildtype Logatchev CA and cell-free broths comprising the variants described in Table 1 were heat-treated at 80 degrees Celsius for 15 minutes as described in Example 1 and references therein. Enzyme activity was measured independently for each variant and the respective enzymatic CA activities of each variant were normalized to protein concentration based on protein yield as determined by SDS-PAGE (Table 2). Each CA variant showed significant WAU activity, clearly indicating that each variant has carbonic anhydrase activity. Variant1, Variant2, and Variant3 showed an increase in Relative WAU activity compared to the wildtype, which indicates improved catalytic efficiency. Because a heat-treatment was applied before measuring the enzyme activity, the improved Relative WAU activity for Variant1, Variant2, and Variant3 is consistent with improved thermal stability of these variants compared to the wildtype. Variant4 also had significant WAU activity, though gave a somewhat lower Relative WAU activity compared to the wildtype, which could be due to somewhat lower catalytic efficiency or lower thermal stability of Variant4 compared to the wildtype.

TABLE 2

| Carbonic anhydrase activity of Logatchev CA and variants. | | |
|---|---|---|
| Carbonic anhydrase | WAU | Relative WAU |
| Logatchev CA (wildtype) | 750 | 100% |
| Variant1 | 790 | 105% |
| Variant2 | 880 | 117% |
| Variant3 | 890 | 119% |
| Variant4 | 650 | 87% |

Example 4

Thermostability of Logatchev CA and Variants Thereof

Thermostability of the recombinant Logatchev CA and variants thereof was determined by thermal shift assay (TSA) at pH 7. TSA evaluations were run with enzyme samples diluted to 0.3 mg/mL in a buffer with the following composition: 100 mM succinic acid, 100 mM HEPES, 100 mM glycine, 150 mM KCl, 1 mM $CaCl_2$, 0.01% Triton X100, pH adjusted to 7. SYPRO Orange dye (Life Technologies S6650) was diluted 101× in Milli-Q water. Diluted enzyme sample (10 μL), assay buffer (10 μL), and dye (10 μL) were mixed together in wells of TSA plates (LightCycler 480 Multiwell plate 96, white, Roche) and covered with optic seal (LightCycler 480 Sealing foil, Roche). Protein melting analysis was conducted at 25-99° C. at 200° C./h in a Roche Lightcycler 480 II machine running Roche LightCycler 480 software (release 1.5.0 SP4). All samples were analyzed in duplicate. The reported readout is $T_m$, defined as the midpoint value of the protein melting curves.

The thermostability of the Logatchev CA is maintained for Variant1 and Variant2, whereas there is a decrease for Variant3 and Variant4 (Table 3). Although the midpoint melting temperature of variant Variant3 is slightly lower compared to the wildtype, the relative WAU activity (Example 3) was higher, indicating the substitutions provided an efficiency improvement with limited impact on thermostability.

TABLE 3

| Thermostability by TSA; melting temperature ($T_m$) of wildtype and variants at pH 7 determined by TSA. | |
|---|---|
| Carbonic anhydrase | $T_m$ |
| Logatchev CA (wildtype) | 91° C. |
| Variant1 | 91° C. |
| Variant2 | 91° C. |
| Variant3 | 86° C. |
| Variant4 | 84° C. |

Example 5

Thermostability of the Logatchev CA in a High Ionic Strength Alkaline Solvent

High ionic strength alkaline solvents are used in $CO_2$ capture applications. The thermostability of the recombinant Logatchev CA was determined by Differential Scanning Calorimetry (DSC). Samples were diluted to approximately 1 mg/mL in 1.5 M Glycine buffer at pH 8, 9 or 10 and the thermal midpoint ($T_m$) was determined by scanning from 20-120° C. at 200° C. per hour. The results (Table 4) show that the Logatchev CA (SEQ ID NO: 5) has very good thermostability, with $T_m$>90° C., across the full pH range tested, and thermostability was highest at pH 10.

TABLE 4

| Thermostability by DSC; melting temperature ($T_m$) of Logatchev CA in 1.5M Glycine at pH 8, 9 or 10 determined by DSC. | | |
|---|---|---|
| Solvent | pH | $T_m$ |
| 1.5M Glycine | pH 8 | 92.2 |
| | pH 9 | 91.1 |
| | pH 10 | 103.6 |

Example 6

Specific Activity of Logatchev CA Compared to *Persephonella marina* DSM 14350 CA Specific activity is a measure of enzyme activity per physical quantity of enzyme present in a sample. In order to improve the accuracy of enzyme quantity determination, samples of Logatchev CA (SEQ ID NO: 5) and *Persephonella marina* DSM 14350 CA described in WO 2012/025577 were first purified to remove contaminating materials. Enzyme quantity was then determined via Amino Acid analysis, a technique which quantifies amino acids present in a sample and aligns this with the underlying enzyme amino acid sequence in order to quantify enzyme amount. Enzyme activity was measured using a method analogous to that described in Example 3, but modified in order to use a spreadsheet program to calculate reaction rates for catalyzed and uncatalyzed reactions in order to determine the activity of the enzyme (as described in US 2016/0010142).

The specific activity of Logatchev CA was determined to be 1.4 fold higher than *P. marina* CA, indicating that less total Logatchev CA would be required to achieve a target enzyme activity relative to *P. marina* CA.

Example 7

Stable Activity Enhancement of Logatchev CA in the Presence of Salt

Protein stability and activity can be improved by the presence of ions. Aqueous samples containing Logatchev CA (SEQ ID NO: 5) were diluted 10-fold in 0.3M NaCl and incubated at ambient temperature (approximately 20° C.) or 40° C. for one week. Samples were removed at the start of the test period (Day 0) and on Days 1, 2, 5, and 7. CA activity was measured using a method as described in Example 6. Percent Activity Remaining was calculated relative to the activity of the Day 0 sample for each temperature treatment. The results (Table 5) show that samples incubated in the presence of 0.3 M NaCl achieved a stable activity enhancement, evident by an increased Percent Activity Remaining, compared to the Day 0 reference. Therefore, the activity of Logatchev CA at different temperatures was improved in the presence of 0.3M NaCl.

TABLE 5

| Activity Enhancement. Percent Activity Remaining of Logatchev CA over time in the presence of 0.3M NaCl addition, at ambient temperature and 40° C. | | |
|---|---|---|
| | Percent Activity Remaining | |
| Time (d) | Ambient | 40° C. |
| 0 | 100% | 100% |
| 1 | 145% | 144% |
| 2 | 141% | 134% |

TABLE 5-continued

Activity Enhancement. Percent Activity Remaining of Logatchev CA over time in the presence of 0.3M NaCl addition, at ambient temperature and 40° C.

| | Percent Activity Remaining | |
|---|---|---|
| Time (d) | Ambient | 40° C. |
| 5 | 130% | 137% |
| 7 | 136% | 145% |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A nucleic acid construct comprising a polynucleotide encoding a polypeptide having carbonic anhydrase activity, wherein the polynucleotide is operably linked to one or more heterologous control sequences that direct production of the polypeptide in an expression host, and wherein the polypeptide comprises an amino acid sequence having at least 90% sequence identity to the mature polypeptide of SEQ ID NO: 2, or a fragment thereof, wherein said sequence or fragment has carbonic anhydrase activity.

2. A recombinant host cell comprising the nucleic acid construct of claim 1.

3. A method of producing a polypeptide having carbonic anhydrase activity, the method comprising cultivating the host cell of claim 2 under conditions conducive for production of the polypeptide.

4. The method of claim 3, further comprising recovering the polypeptide.

5. The nucleic acid construct of claim 1, wherein the amino acid sequence has at least 95% sequence identity to the mature polypeptide of SEQ ID NO: 2.

6. The nucleic acid construct of claim 1, wherein the amino acid sequence has at least 97% sequence identity to the mature polypeptide of SEQ ID NO: 2.

7. The nucleic acid construct of claim 1, wherein the polypeptide having carbonic anhydrase activity consists of the mature polypeptide of SEQ ID NO: 2.

8. The nucleic acid construct of claim 3, wherein the polypeptide having carbonic anhydrase activity is a variant comprising a substitution, deletion, or insertion of one or more amino acids of the mature polypeptide of SEQ ID NO: 2.

9. The nucleic acid construct of claim 1, wherein the amino acid sequence is a fragment of the mature polypeptide of SEQ ID NO: 2.

10. A method of producing a polypeptide having carbonic anhydrase activity, said method comprising:

(i) cultivating a host cell comprising a polynucleotide encoding a polypeptide having carbonic anhydrase activity under conditions conducive for production of the polypeptide; and (ii) recovering the polypeptide having carbonic anhydrase activity, wherein the polypeptide comprises an amino acid sequence having at least 90% sequence identity to the mature polypeptide of SEQ ID NO: 2, wherein said sequence has carbonic anhydrase activity.

11. The method of claim 10, wherein the sequence has at least 95% sequence identity to the mature polypeptide of SEQ ID NO: 2.

12. The method of claim 10, wherein the sequence has at least 97% sequence identity to the mature polypeptide of SEQ ID NO: 2.

13. The recombinant host cell of claim 2, wherein the amino acid sequence has at least 95% sequence identity to the mature polypeptide of SEQ ID NO: 2.

14. The recombinant host cell of claim 2, wherein the amino acid sequence has at least 97% sequence identity to amino acids 1 to 226 the mature polypeptide of SEQ ID NO: 2.

15. The recombinant host cell of claim 2, wherein the polypeptide having carbonic anhydrase activity comprises or consists of the mature polypeptide of SEQ ID NO: 2.

* * * * *